(12) United States Patent
Geng

(10) Patent No.: US 7,349,104 B2
(45) Date of Patent: Mar. 25, 2008

(54) SYSTEM AND A METHOD FOR THREE-DIMENSIONAL IMAGING SYSTEMS

(75) Inventor: Z. Jason Geng, Rockville, MD (US)

(73) Assignee: Technest Holdings, Inc., Boston, MA (US)

( * ) Notice: Subject to any disclaimer, the term of this patent is extended or adjusted under 35 U.S.C. 154(b) by 493 days.

(21) Appl. No.: 10/973,533

(22) Filed: Oct. 25, 2004

(65) Prior Publication Data

US 2005/0088529 A1    Apr. 28, 2005

Related U.S. Application Data

(60) Provisional application No. 60/514,177, filed on Oct. 23, 2003.

(51) Int. Cl.
*G01B 11/24* (2006.01)
*G01J 3/46* (2006.01)

(52) U.S. Cl. .......................... 356/603; 356/403
(58) Field of Classification Search ......... 356/601–603
See application file for complete search history.

(56) References Cited

U.S. PATENT DOCUMENTS

| | | | | |
|---|---|---|---|---|
| 4,648,717 A | * | 3/1987 | Ross et al. | 356/610 |
| 5,903,380 A | * | 5/1999 | Motamedi et al. | 359/224 |
| 6,341,016 B1 | * | 1/2002 | Malione | 356/603 |
| 6,700,669 B1 | * | 3/2004 | Geng | 356/603 |
| 6,937,348 B2 | * | 8/2005 | Geng | 356/603 |
| 2003/0039388 A1 | * | 2/2003 | Ulrich et al. | 382/145 |
| 2004/0145753 A1 | * | 7/2004 | Lim et al. | 356/602 |

* cited by examiner

*Primary Examiner*—Tarifur Chowdhury
*Assistant Examiner*—Tara S. Pajoohi
(74) *Attorney, Agent, or Firm*—Steven L. Nichols; Rader, Fishman & Grauer PLLC

(57) ABSTRACT

A method for acquiring a surface profile 3D data set of an object includes illuminating a surface of the object with a sequence of multiple rainbow projection (MRP) structural light patterns, capturing light reflected from the object, and calculating 3D data (X, Y, Z) for each visible point on the object based upon triangulation mathematical principles of the captured reflected light.

22 Claims, 17 Drawing Sheets

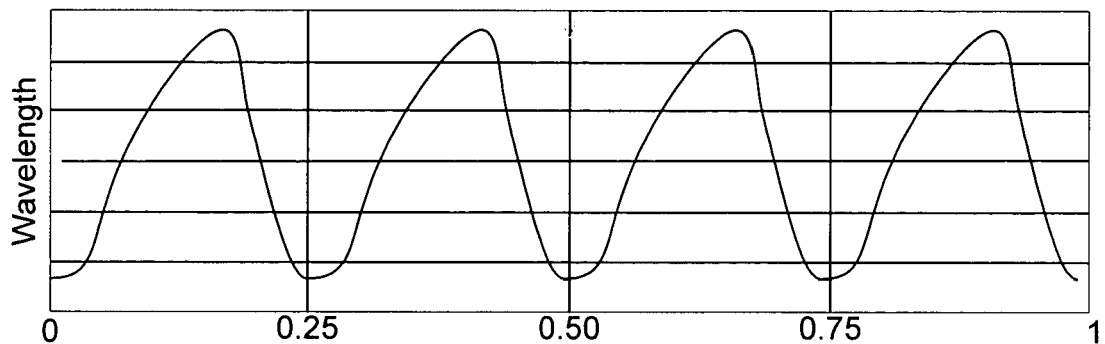
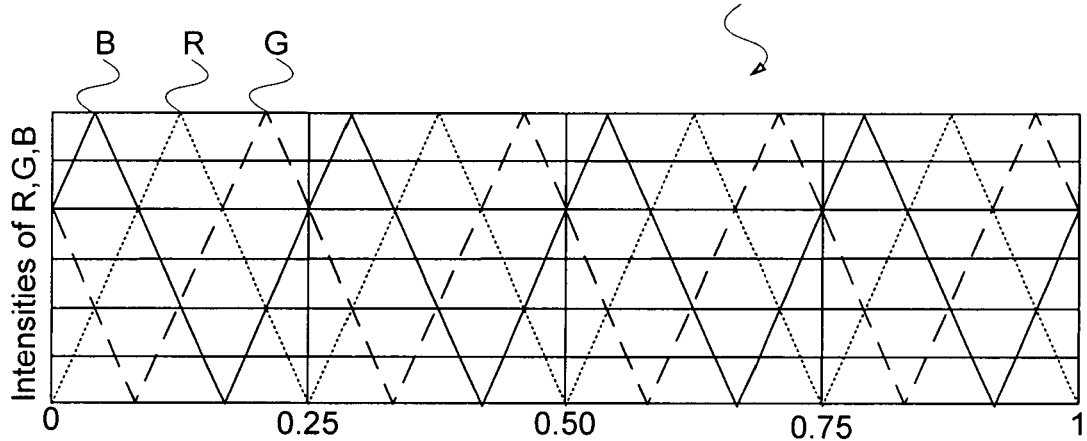
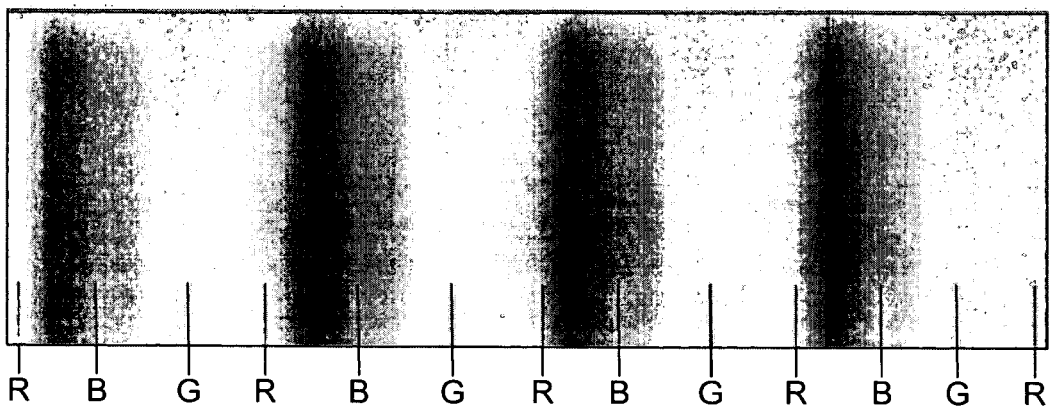
Fig. 3

SYSTEM AND A METHOD FOR THREE-DIMENSIONAL IMAGING SYSTEMS

RELATED APPLICATIONS

The present application claims priority under 35 U.S.C. § 119(e) from the following previously-filed Provisional Patent Application, U.S. Application No. 60/514,177, filed Oct. 23, 2003 by Geng, entitled "Method and Apparatus of 3D Imaging Systems" which is incorporated herein by reference in its entirety.

BACKGROUND

High-speed three-dimensional (3D) imaging is an increasingly important function in advanced sensors in both military and civilian applications. For example, high-speed 3D capabilities offer many military systems with greatly increased capabilities in target detection, identification, classification, tracking, and kill determination. As a further example, real time 3D imaging techniques also have great potential in commercial applications, ranging from 3D television, virtual reality, 3D modeling and simulation, Internet applications, industrial inspection, vehicle navigation, robotics and tele-operation, to medical imaging, dental measurement, as well as apparel and footwear industries, just to name a few.

A number of three dimensional surface profile imaging methods and apparatuses described in U.S. Pat. Nos. 5,675,407; U.S. Pat. No. 6,028,672; and U.S. Pat. No. 6,147,760; the disclosures of which is incorporated herein by reference in their entireties, conduct imaging by projecting light through a linear variable wavelength filter (LVWF), thereby projecting light having a known, spatially distributed wavelength spectrum on the objects being imaged. The LVWF is a rectangular optical glass plate coated with a color-filtering film that gradually varies in color, (i.e., wavelength). If the color spectrum of a LVWF is within the visible light region, one edge of the filter rectangle may correspond to the shortest visible wavelength (i.e. blue or violet) while the opposite edge may correspond to the longest visible wavelength, (i.e. red). The wavelength of light passing through the coated color-filtering layer is linearly proportional to the distance between the position on the filter glass where the light passes and the blue or red edge. Consequently, the color of the light is directly related to the angle θ, shown in FIG. 1, at which the light leaves the rainbow projector and LVWF.

Referring to FIGS. 1 and 2 in more detail, the imaging method and apparatus is based on the triangulation principle and the relationship between a light projector (100) that projects through the LVWF (101), a camera (102), and the object or scene being imaged (104). As shown in FIG. 1, a triangle is uniquely defined by the angles theta (θ) and alpha (α), and the length of the baseline (B). With known values for θ, α, and β, the distance (i.e., the range R) between the camera (102) and a point Q on the object's surface can be easily calculated. Because the baseline B is predetermined by the relative positions of the light projector (100) and the camera (102), and the value of a can be calculated from the camera's geometry, the key to the triangulation method is to determine the projection angle, θ, from an image captured by the camera (102) and more particularly to determine all θ angles corresponding to all the visible points on an object's surface in order to obtain a full-frame 3D image in one snapshot.

FIG. 2 is a more detailed version of FIG. 1 and illustrates the manner in which all visible points on the object's surface (104) are obtained via the triangulation method. As can be seen in the figure, the light projector (100) generates a fan beam of light (200). The fan beam (200) is broad spectrum light (i.e., white light) which passes through the LVWF (101) to illuminate one or more three-dimensional objects (104) in the scene with a pattern of light rays possessing a rainbow-like spectrum distribution. The fan beam of light (200) is composed of multiple vertical planes of light (202), or "light sheets", each plane having a given projection angle and wavelength. Because of the fixed geometric relationship among the light source (100), the lens of the camera (102), and the LVWF (101), there exists a one-to-one correspondence between the projection angle (θ) of the vertical plane of light and the wavelength (λ) of the light ray. Note that although the wavelength variations are shown in FIG. 2 to occur from side to side across the object (104) being imaged, it will be understood by those skilled in the art that the variations in wavelength could also be made from top to bottom across the object (104) or scene being imaged.

The light reflected from the object (104) surface is then detected by the camera (102). If a visible spectrum range LVWF (400-700 nm) is used, the color detected by the camera pixels is determined by the proportion of its primary color Red, Green, and Blue components (RGB). The color spectrum of each pixel has a one-to-one correspondence with the projection angle (θ) of the plane of light due to the fixed geometry of the camera (102) lens and the LVWF (101) characteristics. Therefore, the color of light received by the camera (102) can be used to determine the angle θ at which that light left the light projector (100) through the LVWF (101).

As described above, the angle α is determined by the physical relationship between the camera (102) and the coordinates of each pixel on the camera's imaging plane. The baseline B between the camera's (102) focal point and the center of the cylindrical lens of the light projector (100) is fixed and known. Given the value for angles α and θ, together with the known baseline length B, all necessary information is provided to easily determine the full frame of three-dimensional range values (x,y,z) for any and every visible spot on the surface of the objects (104) seen by the camera (102).

While the camera (102) illustrated in FIG. 2 effectively produces full frame three-dimensional range values for any and every visible spot on the surface of an object (104), the camera (102) also requires a high signal-to-noise (S/N) ratio, a color sensor, and an LVWF (101) with precision spectral variation, all of which is expensive to achieve. Consequently, there is a need in the art for an inexpensive yet high speed three dimensional camera.

SUMMARY

A method for acquiring a surface profile 3D data set of an object includes illuminating a surface of the object with a sequence of multiple rainbow projection (MRP) structural light patterns, capturing light reflected from the object, and calculating 3D data (X, Y, Z) for each visible point on the object based upon triangulation mathematical principles of the captured reflected light.

BRIEF DESCRIPTION OF THE DRAWINGS

The accompanying drawings illustrate various embodiments of the present system and method and are a part of the specification. The illustrated embodiments are merely examples and do not limit the scope of the claims.

FIG. 3 is a plurality of simplified charts illustrating the characteristics of a multiple rainbow projection (MRP) pattern, according to one exemplary embodiment.

Throughout the drawings, identical reference numbers designate similar but not necessarily identical elements.

DETAILED DESCRIPTION

The present specification discloses a system and a method for performing 3D surface imaging. More specifically, the present specification provides a number of exemplary systems and methods for using sequential frame image acquisitions to obtain equivalent rainbow projection information such that a 3D profile of the object surface can be computed accurately. Specific details of the systems and methods will be provided herein.

Figure 1:
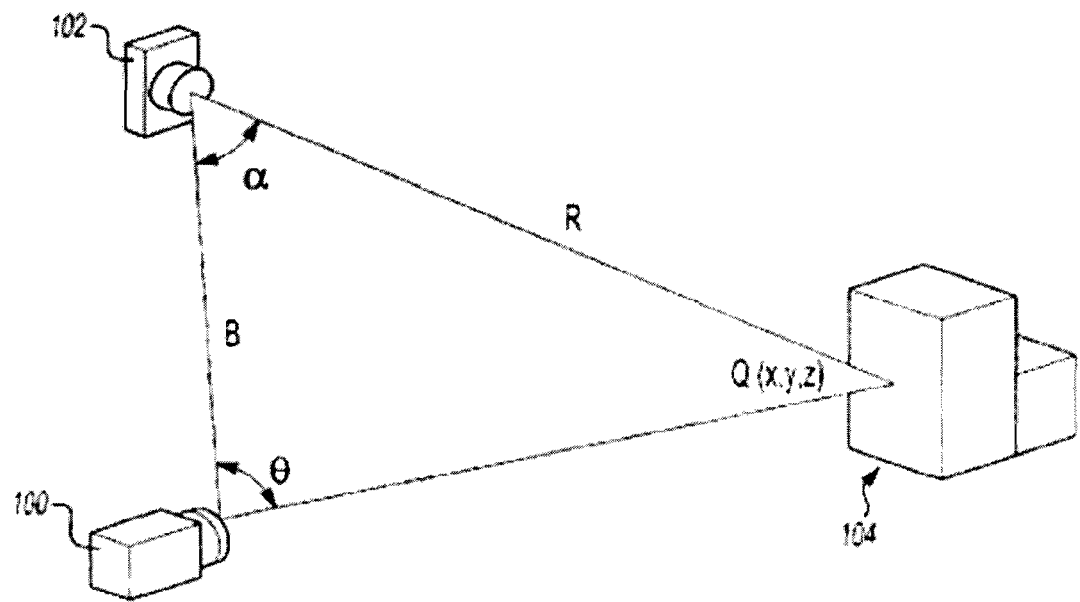
FIG. 1 is a simplified block diagram illustrating a triangulation principle according to one exemplary embodiment.
Figure 2:
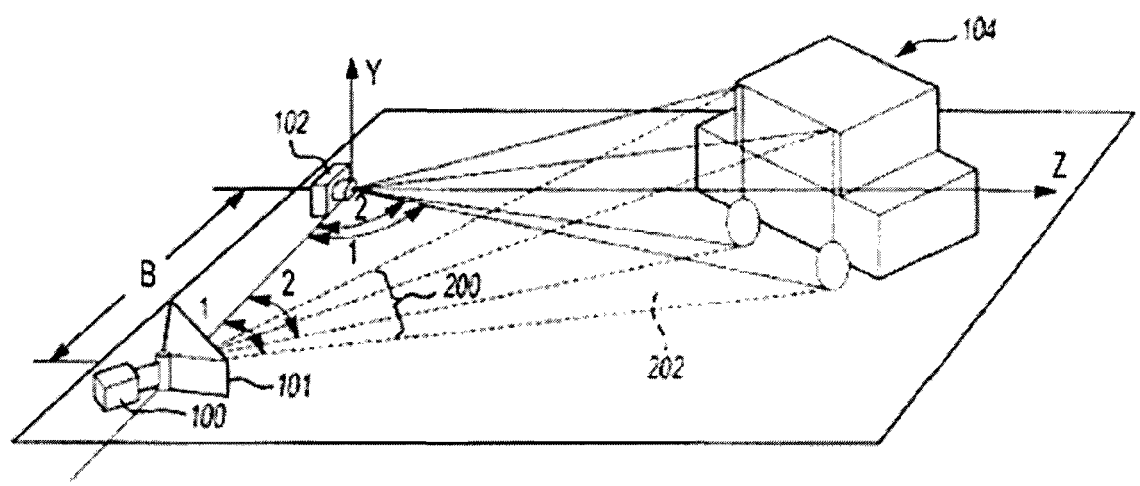
FIG. 2 is a block diagram illustrating a triangulation principle according to one exemplary embodiment.

As used in the present specification and in the appended claims, the phrase "CCD" or "charge-coupled device" is meant to be understood as any light-sensitive integrated circuit that stores and displays the data for an image in such a way that each pixel (picture element) in the image is converted into an electrical charge, the intensity of which is related to a color in the color spectrum. Additionally, the term "trigger" is meant to be understood as an event or period of time during which a projection or sensing event is performed. "Cross-talk" refers to any interference between projection patterns, whether projected from a single projector or multiple projectors. Additionally the term "Philips prism" is a term of art referring to an optical prism having tilted dichroic surfaces. Also, the term "monochromatic" refers to any electromagnetic radiation having a single wavelength. The term "Rainbow-type image" or "Rainbow-type camera" is meant to be understood as an image or a camera configured to collect an image that may be used to form a three-dimensional image according to the triangulation principles illustrated above with respect to FIGS. 1 and 2.

In the following description, for purposes of explanation, numerous specific details are set forth in order to provide a thorough understanding of the present system and method for performing 3D surface imaging using sequential frame image acquisitions. It will be apparent, however, to one skilled in the art that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As noted previously, the Rainbow 3D Camera includes a number of unique and advantageous features. The Rainbow 3D system has an inherent ability of capturing full field 3D images. Using a standard CCD camera, a 2D image (or snapshot) can be obtained in 0.001 second, and a stream of 3D images can be generated at a rate of 30 frames per second without any interpolation. This feature facilitates many real-time 3D imaging applications.

Additionally, the Rainbow 3D concept is superior to other 3D digitizers in terms of obtaining high-resolution 3D images. Conventional 3D laser scanners, for example, project sheets of light. The deformation of light stripes provides 3D measurements along the line. This scheme, however, suffers poor spatial resolution due to the width of pattern stripes. Not only the spatial resolution is low, but also it is not a single snapshot operation. Rainbow 3D camera totally eliminates these drawbacks. The projected rainbow pattern is a continuous spatial function providing a theoretically infinite spatial resolution that is practically limited only by the spatial and spectral resolution of the CCD image sensor. Moreover, the Rainbow 3D system can be designed with a safety level comparable to a conventional intraoral video camera with built-in light source, and poses no hazards for intraoral clinical applications if used professionally for its intended purpose. It is, therefore, completely eye-safe.

Also, unlike many scanning laser based 3D systems, the traditional Rainbow 3D camera has no mechanical moving parts, therefore the mechanical design becomes very simple and reliable. The Rainbow 3D Camera system can also provide normal 2D intensity image using the same imager. The 3D images and the 2D intensity images, both acquired by the same camera, provide complementary information that greatly facilitates surface feature analysis and data fusion tasks. In addition to using visible light sources, it is possible to use Infrared (IR) or Ultra-violet (UV) light sources with suitable wavelength sensitive detectors for special applications with a minor design modification of this 3D probe.

Further, surface color of objects has no effect on 3D measurement accuracy of the traditional Rainbow 3D Camera. Under the Rainbow projection, the spectral composition at any single surface point contains only single wavelength, therefore, any surface point only variation of surface color only affects the intensity of detected signal, not its wavelength. Using a normalization scheme, such effect can be totally eliminated in the Rainbow 3D scheme.

While the Rainbow 3D Camera technology provides a solid foundation for building various 3D cameras capable of acquiring accurate 3D shape of objects, measurement accuracy is somewhat limited due to the optical baseline used.

In contrast to the traditional Rainbow 3D Camera technology, the present system and method incorporates a structured light projector design, referred to herein as the multi-rainbow projection (MRP) that enables higher 3D measurement accuracy with smaller optical baseline. Referring to the principle of the Rainbow 3D Camera, there is a one-to-one corresponding relationship between the wavelength of a light sheet and its projection angle in the original design. This rainbow projection pattern is referred to herein as the Single Rainbow Projection (SRP) illumination. Based on this one-to-one relationship, a $(\omega, \theta)$ lookup table can be established for color match operation. Error sensitivity analysis reveals that the accuracy of color match operation used in the traditional Rainbow 3D camera scheme has a major effect on the accuracy of 3D images. The accuracy of color match, in turn, is significantly determined by the color variation rate of the projected light pattern. Consequently, the present system and method employs the "Multi-Rainbow Projection (MRP)" concept, as shown, for example, in FIG. 3. Rather than modifying the projection wavelength in a single cycle, the present system and method incorporates a projection pattern that varies the wavelength of the projection pattern several times across the entire field of view. Consequently, the present MRP pattern (300), illustrated in FIG. 3, illuminates a desired scene with improved wavelength variation rate thereby achieving improved sensitivity in color matching. Improved sensitivity in color matching results in an improvement of the accuracy of 3D measurements as will be described in further detail below.

FIG. 3 graphically illustrates the characteristics of the MRP pattern, according to one exemplary embodiment. As illustrated in FIG. 3, the multiple rainbow projection pattern has a spatial displacement (310) that corresponds to the varying intensities (320) of the red (R), green (G), and blue (B) wavelengths. These varying intensities are then combined to produce the MRP pattern (300). As illustrated in FIG. 3, it is evident that for a given wavelength, there are multiple possible projection angles. Consequently, the MRP eliminates the one-to-one corresponding relationship used by the Rainbow 3D camera. Therefore, additional procedures are used by the present system and method to distinguish the correct projection angle from multiple candidates resulting from the one-to-many lookup table illustrated by FIG. 3.

Figure 4:
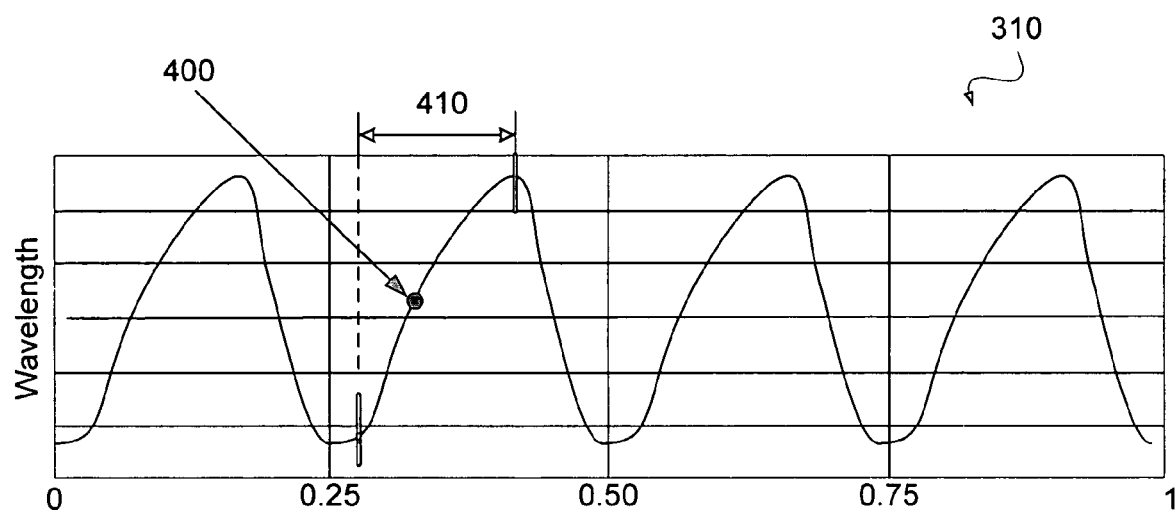
FIG. 4 is a simplified chart illustrating an improved color matching scheme for an MRP pattern, according to one exemplary embodiment.

According to one exemplary embodiment, ambiguity in the color match operation is reduced by reducing the searching range in the color space to cover only one cycle of rainbow variation, as illustrated in FIG. 4. Although color-angle lookup table has the one-to-many mapping property in MRP, the present exemplary embodiment restricts the search space to a single cycle of rainbow variation to achieve a one-to-one correspondence. Consequently, within one cycle of the rainbow projection, the solution to color match becomes unique, or one-to-one.

As illustrated in FIG. 4, the searching range (410) in the color space (310) is reduced to cover only one cycle of rainbow variation. While this exemplary method produces a one-to-one correspondence, the outcome of the search relies heavily upon the initial condition or initial point of the search (400). If a search starts within a search range (410) of the actual solution, it can achieve a correct result. If, however, a search starts at an initial point of search (400) located away from the proper solution, it may produce a wrong answer.

Consequently, the present system and method uses an adaptive control scheme to determine the initial search point. According to this exemplary embodiment, when using a local search method in a one-to-many MRP, using an adaptive control scheme increases the chance of identifying a good initial point of search (400). According to one exemplary embodiment, the initial point of search (400) is determined by a previously obtained correct match point adjacent to it. An adjacent previously obtained correct match point is chosen because a large portion of the surface of a physical object is typically continuous, thus the projected color is similar and the projection angle should be very similar.

Design and Implementation of the Multi-Rainbow Projection Module

According to one exemplary embodiment, the Multi-Rainbow Projector is a key component in the design of a 3D camera that produces multiple cycles of rainbow-like illumination on the object surface with spatially varying wavelength for 3D imaging, according to the present exemplary system and method. Two possible approaches to producing multi-rainbow projection for 3D camera include using a custom-made multi-rainbow filter or using multiple monochromatic filters with prism beamsplitters.

Figure 5:
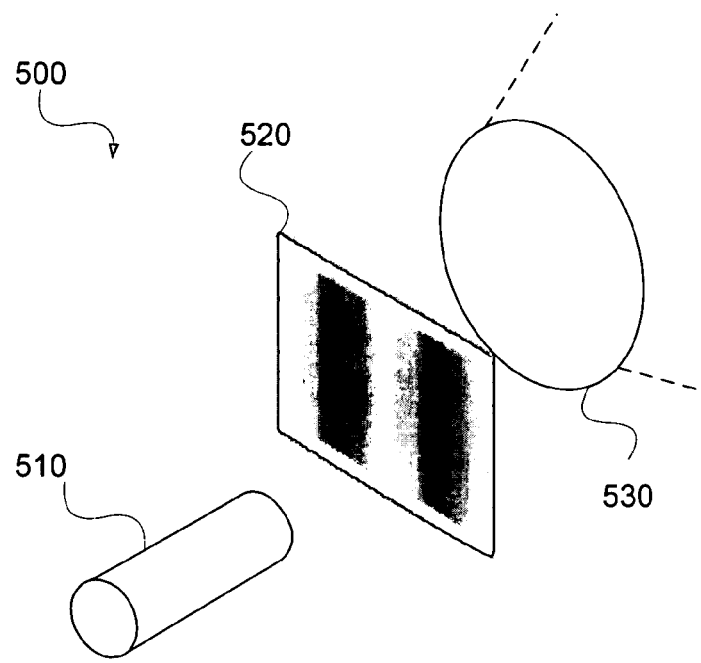
FIG. 5 is a simple block diagram illustrating an exemplary system for generating an MRP pattern using a multi-rainbow filer, according to one exemplary embodiment.

According to a first exemplary embodiment, the MRP projector (500) includes a white light source (510) configured to transmit white light through a multi-rainbow filter (520) and through projection optics (530), as illustrated in FIG. 5. As illustrated in FIG. 5, the use of a custom-made multi-rainbow filter is mechanically simple and incorporates few parts, thereby enhancing durability. According to one exemplary embodiment, the multi-rainbow filter (520) can achieve a Spectral Error Band (SEB) of between approximately 20 to 9 nm. According to this exemplary embodiment, the SEB is the limiting factor to the accuracy of the MRP projector (500) because it may affect the accuracy of color matching as discussed previously.

According to a second exemplary embodiment, the MRP projector incorporates monochromic filters in conjunction with prism beamsplitters to produce the desired MRP. By comparison, the incorporation of the monochromic components will reduce the overall cost of the MRP projector. FIGS. 6 through 9 will now be described in further detail to explain the second exemplary embodiment.

Figure 6:
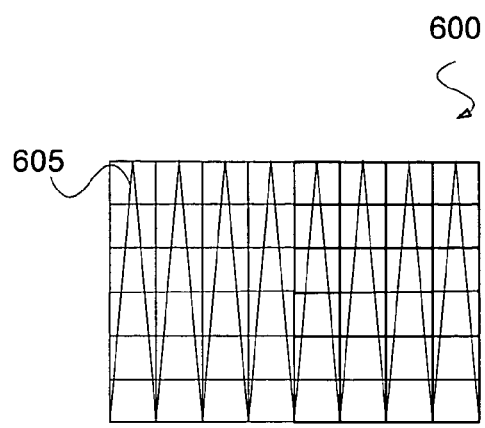
FIG. 6 is a simplified chart illustrating a monochromatic pattern filter, according to one exemplary embodiment.
Figure 7:
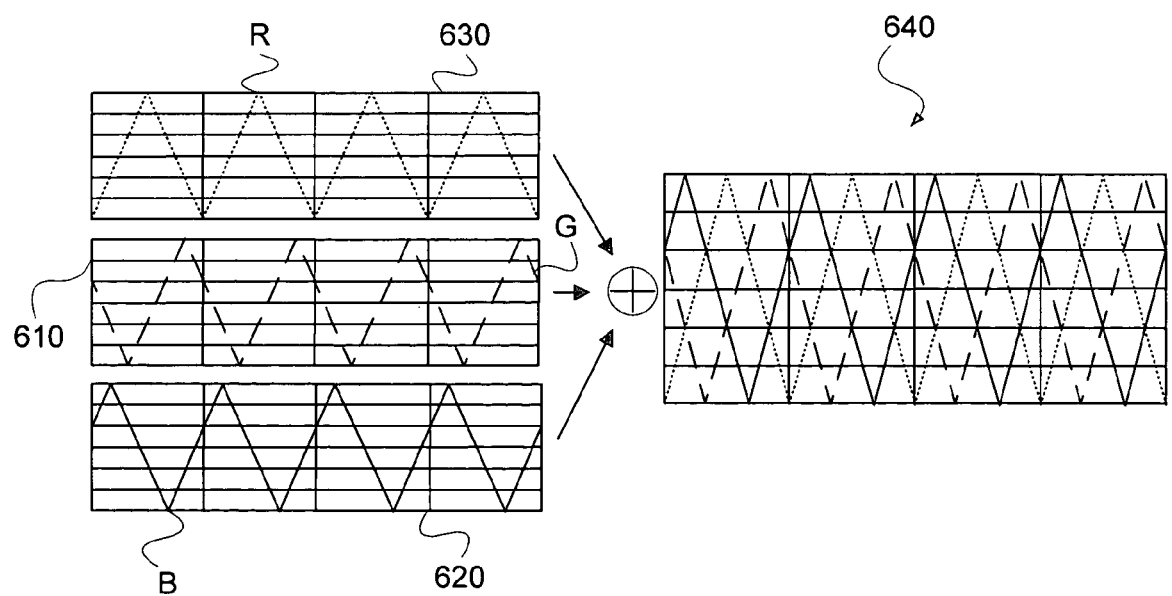
FIG. 7 is a chart illustrating a method for forming an MRP pattern, according to one exemplary embodiment.

FIG. 6 illustrates a monochromatic pattern filter (600), according to one exemplary embodiment. As illustrated in FIG. 6, the monochromatic pattern filter (600) has a linear variation with multiple periods of cycles. As illustrated in FIG. 7, there is a 120 degree phase shift between three filters, a first monochromatic filter (610) combined with a first color, a second monochromatic filter (620) combined with a second color, and a third monochromatic filter (630) combined with a third color. As illustrated in FIG. 7, the pattern filters (610, 620, 630) may be combined to form a composite (640) of individual color projection patterns that produce an MRP pattern.

Figure 8:
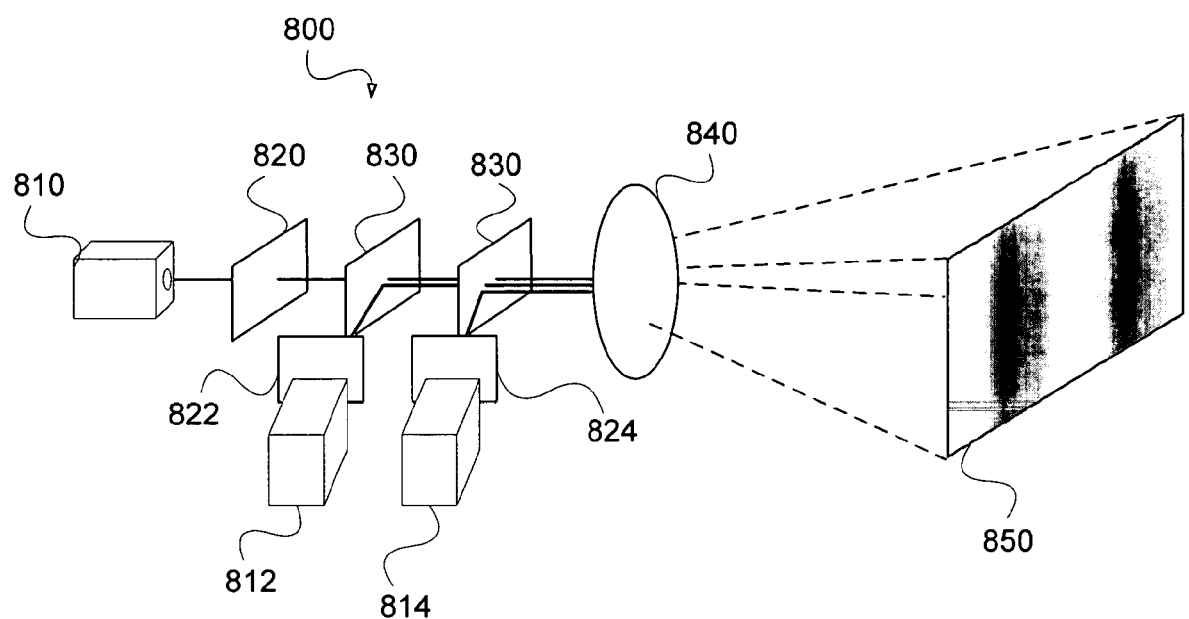
FIG. 8 is a simple block diagram illustrating a MRP system, according to one exemplary embodiment.
Figure 9:
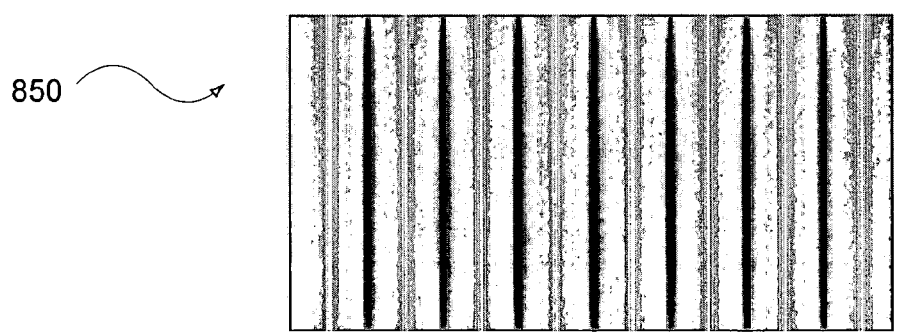
FIG. 9 is a simplified diagram illustrating a monochromatic filter design pattern, according to one exemplary embodiment.

FIG. 8 illustrates an MRP projector (800) incorporating the above-mentioned method. As illustrated in FIG. 8, a red light emitting diode (810), a green LED (812), and a blue LED (814) are configured to provide illumination energy which is then passed through a red pattern filter (820), a green pattern filter (822), and a blue pattern filter (824), respectively. AS the illumination energy is passed through the pattern filters (820, 822, 824), a number of prisms (830) with 45-degree beam-splitters are used to combine the light in different colors and phases. After the beam combination is performed by the prisms (830) with 45-degree beam-splitters, the projection optics (840) is able to generate a multi-rainbow projection (850) pattern onto the surface of a desired object. FIG. 9 illustrates a design of monochromic patterns for use in the multi-rainbow projection system, according to one exemplary embodiment.

Figure 10:
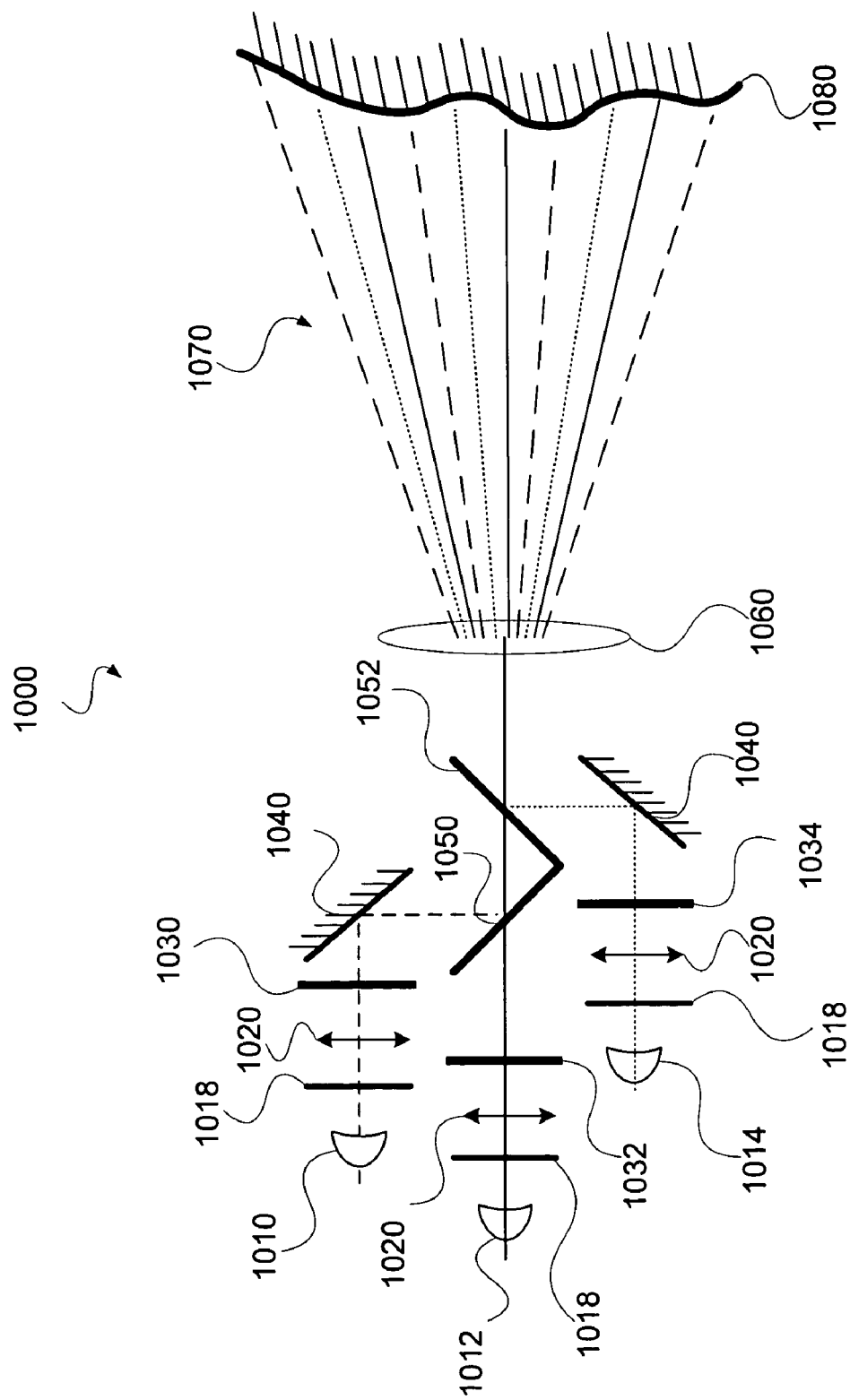
FIG. 10 is a side view illustrating an optics design layout that may be used to produce an MRP pattern, according to one exemplary embodiment.

FIG. 10 illustrates an exemplary optical configuration of an MRP projector (1000), according to one exemplary embodiment. As illustrated in FIG. 10, the MRP projector (1000) includes a red light source (1010), a green light source (1012), and a blue light source (1014). According to one exemplary embodiment, the respective light sources may be any number of light sources including, but in no way limited to, light emitting diodes (LED). Additionally, a diffuser (1018) is disposed adjacent to each of the light sources (1010, 1012, 1014) to diffuse the light produced by the light sources. Additionally, as illustrated in FIG. 10, intermediate optics (1020) may be placed adjacent to the diffusers (1018) to selectively focus the diffused light. After being selectively focused, the diffused light is passed through a red pattern filter (1030), a green pattern filter (1032), or a blue pattern filter (1034) corresponding to the respective light source (1010, 1012, 1014). The filtered light may then be reflected off of any number of reflective surfaces (1040) and passed through a plurality of prisms (1052, 1052) with 45-degree beam-splitters and passed through projection optics (1060) to produce a desired MRP (1070) on the surface of an object to be imaged (1080).

Figure 11:
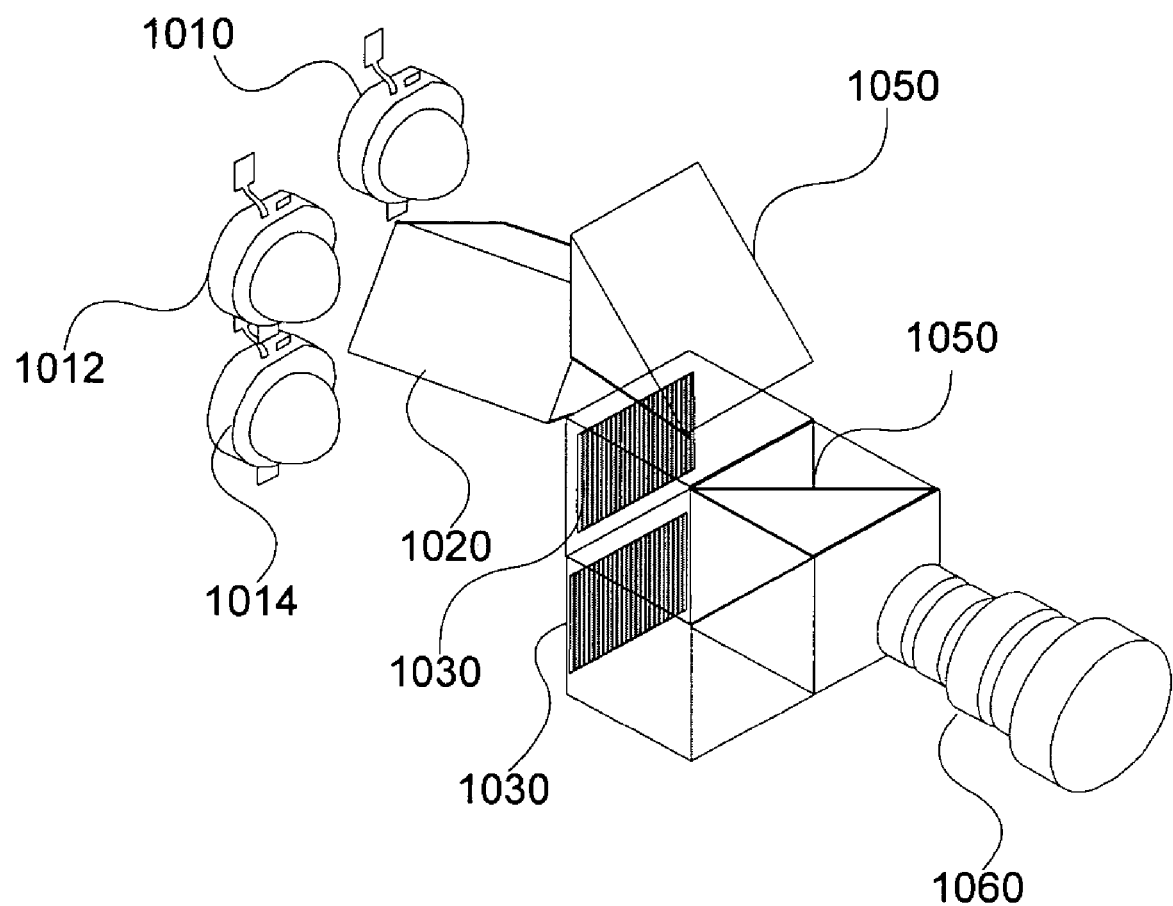
FIG. 11 is a simplified block diagram illustrating a perspective view of an MRP projector, according to one exemplary embodiment.
Figure 12:
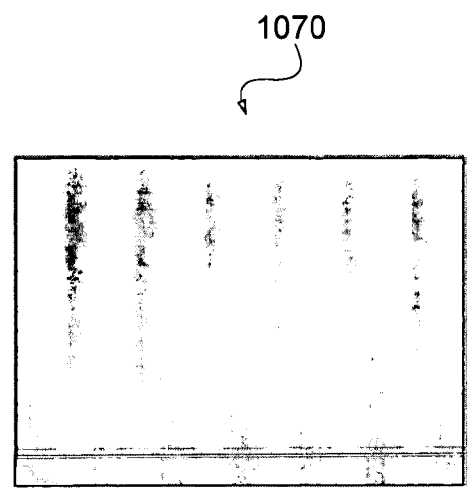
FIG. 12 is a photograph illustrating a multi-rainbow projection pattern from a prototype MRP projector, according to one exemplary embodiment.

FIG. 11 is a screenshot of an exemplary 3D CAD design model of the multi-rainbow projector prototype described above. Similarly, FIG. 12 illustrates an example of the multi-rainbow pattern (1070) produced by the present exemplary embodiment.

Sequential Multi-Rainbow Projection

Figure 13:
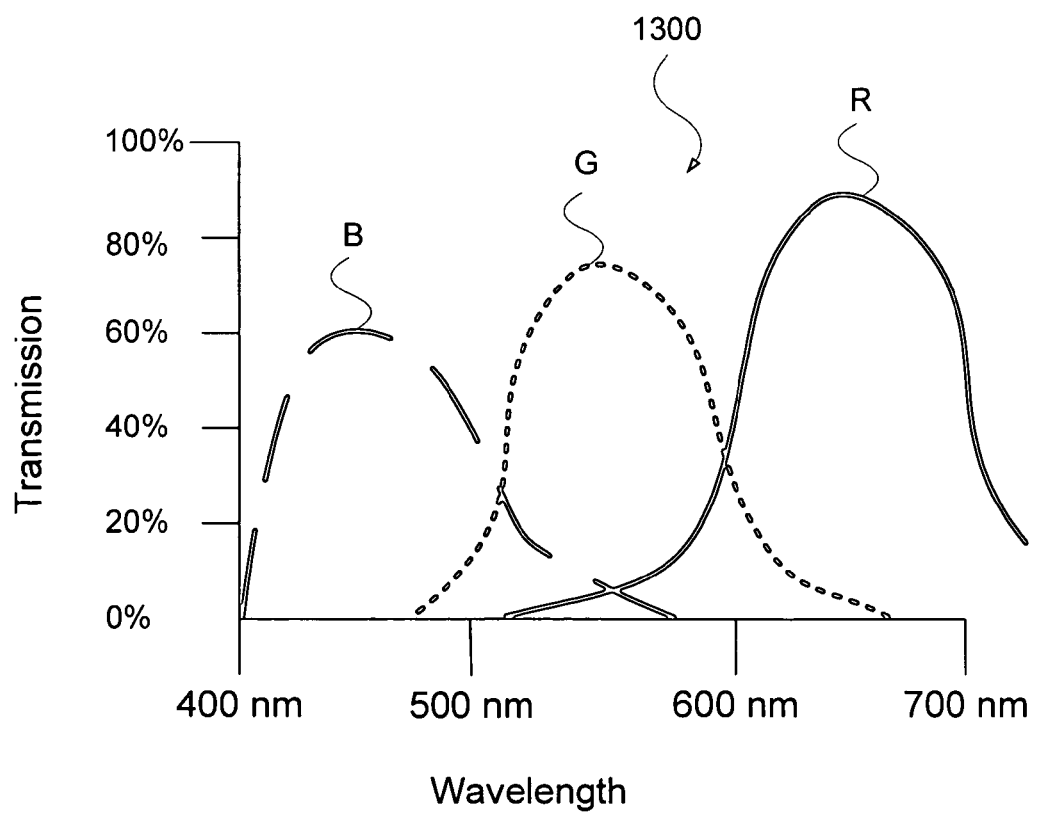
FIG. 13 is a chart illustrating a spectral response of a color CCD camera, according to one exemplary embodiment.

Rainbow light used by the traditional Rainbow 3D Camera is a broad-spectrum projection. According to one exemplary embodiment, a color CCD camera is used to collect the reflection of the rainbow projection from the object surface. A typical spectrum of a CCD camera (1300) is shown in FIG. 13. The sensed spectrum is determined by the ratio of Red, Green, and Blue (RGB) components of a pixel in a color image subsequently acquired by a CCD camera.

Figure 14:
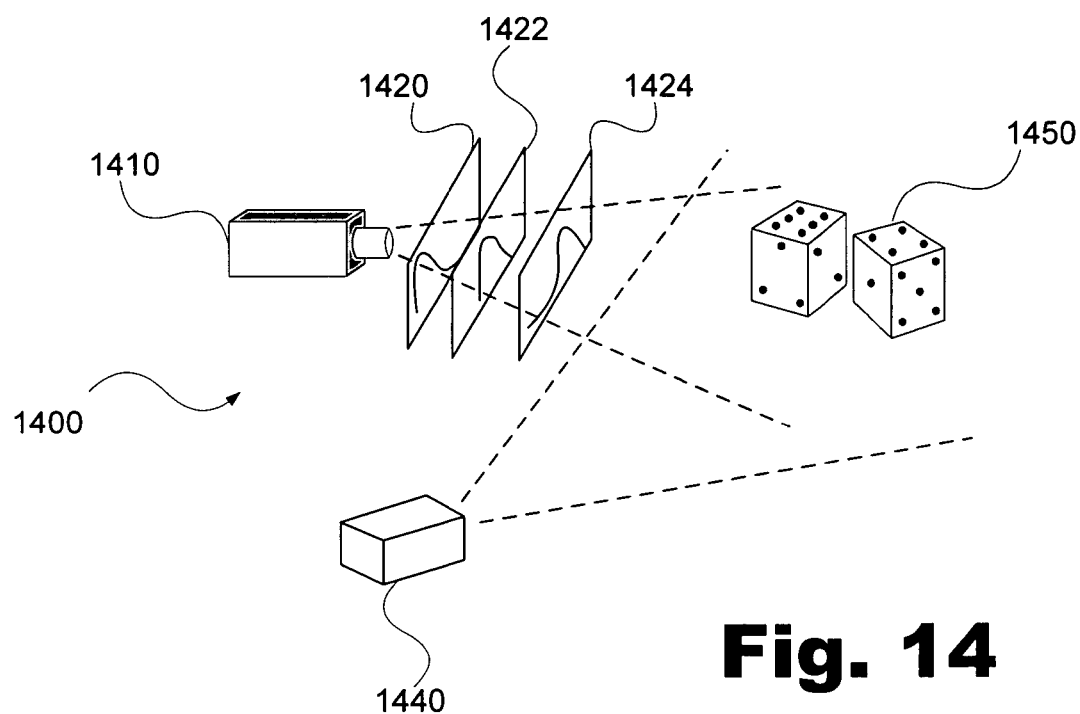
FIG. 14 is a block diagram illustrating a perspective view of a three-dimensional imaging system, according to one exemplary embodiment.

Rather than using an RGB sensor to capture color spectrum image, one exemplary embodiment of the present system and method incorporates a monochromic CCD camera with Red, Green, and Blue filters to capture three separate images, one for each color, and then integrate these three images into a RGB color image. Further, according to one exemplary embodiment illustrated in FIG. 14, a monochromic light projector (1410) with three variable intensity patterns (1420, 1422, 1424) similar to the spectral characteristics of RGB filters of a CCD sensor can be used to provide color spectrum images of a desired object (1450). Three sequential light pattern projections and monochromic image acquisitions are used to obtain one frame of image in a monochromatic CCD camera (1440) that is equivalent to that of a 3D-Rainbow projection, as illustrated in FIG. 14.

With current advancements in CCD sensor technology, monochromic sensors (1440) with a frame rate of 120 frames per second (fps) are off-the-shelf products. Consequently, it is possible to acquire 3D images at 30 fps. This sequential projection technique of using monochromatic CCD camera incorporating a number of filters eliminates the use of color sensors and LVWF. Additionally, the use of CCD optics facilitates the narrow-band projection and image acquisition for each sensor, and consequently, simultaneous acquisition of multiple 3D images from different views using multiple 3D sensors with different spectral wavelengths.

Figure 15:
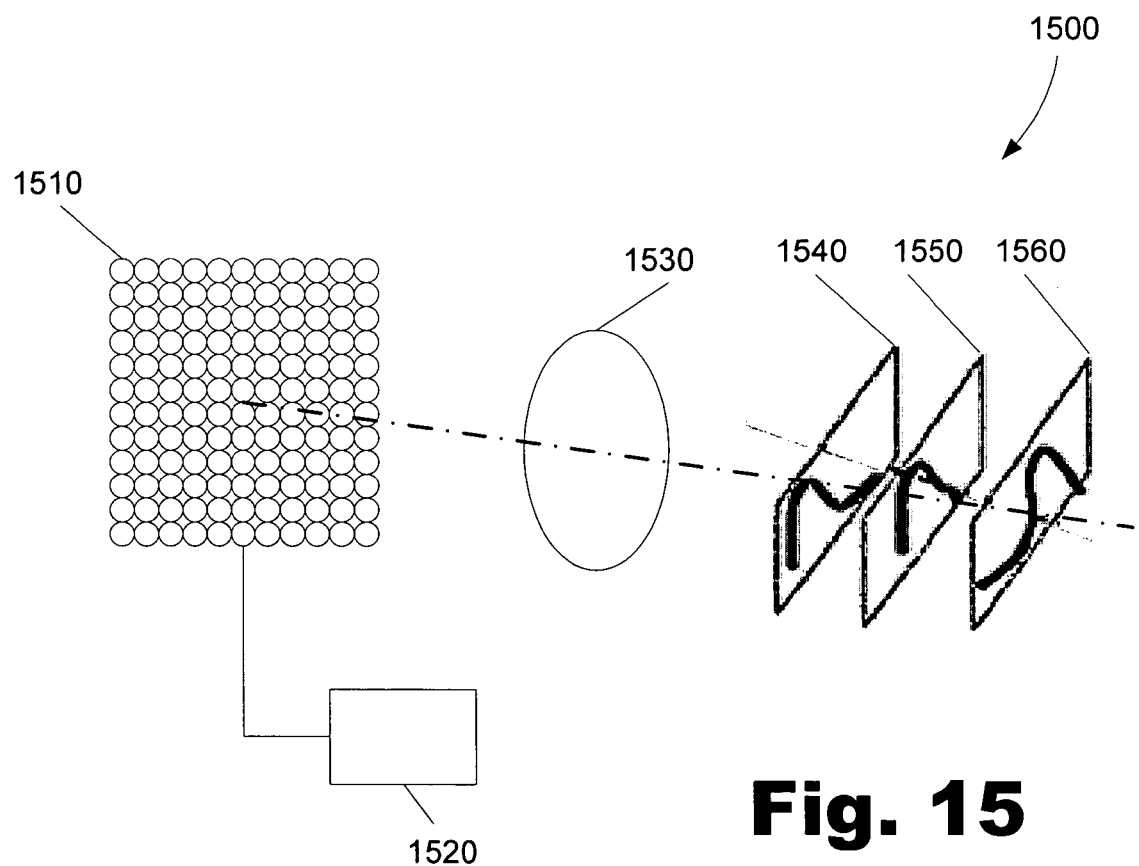
FIG. 15 is a block diagram illustrating a perspective view of an LED array for sequential pattern projection, according to one exemplary embodiment.

In addition to the video projectors previously mentioned, an array of LEDs (1510) can be economically built to produce narrow-band pattern projections (1540, 1550, 1560) as illustrated in FIG. 15. As projection light sources, LEDs have several distinguished advantages including, but in no way limited to, extremely high lighting efficiency: very low current draws (~0.1 A) vs. several Amps for halogen lamps; narrow spectrum band: ~30 nanometer bandwidth, vs. traditional wideband white light projection; Fast response time: nanoseconds vs. seconds for halogen lamps; the ability to synchronize with CCD/CMOS sensor acquisition timing; and good life span: 100,000 hours vs. typical 1000 hours for halogen lamps.

As shown in FIG. 15, a 3D imaging system (1500) may include an array of closely spaced RGB LEDs (1510) formed in a video projector. The spacing of the LEDs (1510) may vary depending on the desired projection patterns. The LEDs (1510) are coupled to a number of electronic drivers (1520) that selectively control the projection of narrow-band pattern projections (1540, 1550, 1560), through projection optics (1530) similar to those described above, and onto a three-dimensional object. By controlling the LED array (1510) with the electronic drivers (1520), the narrow-band pattern projections (1540, 1550, 1560) can be suited to facilitate imaging according to the 3D imaging systems illustrated above. The driver electronics (1520) may control and sequentially vary the intensity of each vertical column of LEDs. To that end, the driver electronics (1520) can include a memory device that pre-stores several designed patterns and perform quick switches among them in the sequential projection operations. Once the narrow-band pattern projections (1540, 1550, 1560) are reflected from the three-dimensional object, they may be sequentially received by imaging optics and sequentially sensed and collected by a 3CCD sensor according to the above-mentioned methods. While the above illustrated example includes varying the intensity of each vertical column of LEDs, the controlled variation of the LEDs may occur on a horizontal row basis or any other desired pattern. Further, the electronic drivers (1520) can be designed to pre-store several designed patterns and perform quick switches among them in the sequential projection operations.

The driver electronics (1520) illustrated in FIG. 15 may also synchronize the projection timing of the LEDs with any number of imaging sensors (CCDs or CMOSs) to achieve a desired optical performance. One of the issues in traditionally structured light 3D imaging systems is that they typically required high brightness to achieve acceptable accuracy. Bright lighting on human faces often affects the comfort level of the human subject. Using the fast response advantage of the LEDs, strong illumination can be projected in a very short amount of time, as short as 1/1000 of a second in one exemplary embodiment. This strong illumination can be synchronized with the timing of an imaging sensor to obtain an acceptable image according to the present system and method. Moreover, the strong illumination in such a short period of time produced by the 3D imaging system (1500) illustrated in FIG. 15 will not be felt by human subjects or cause any harm to the human subjects due to the slow response time of human eyes.

Figure 16:
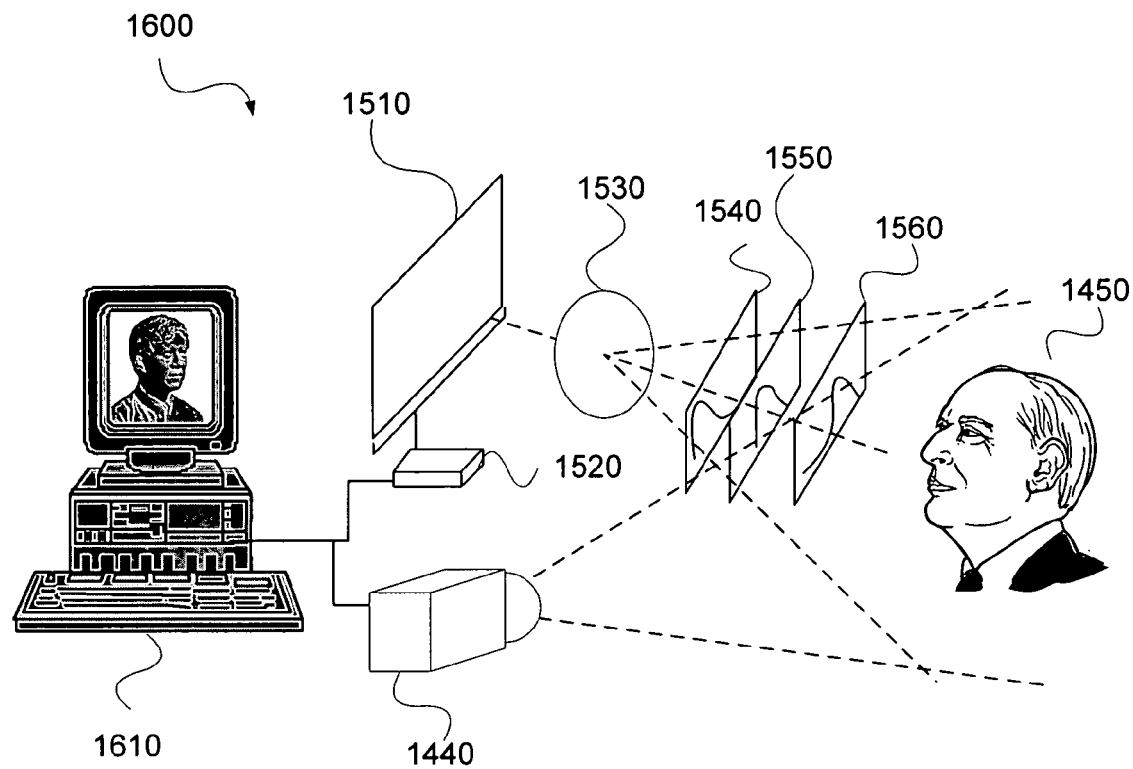
FIG. 16 is a block diagram illustrating a perspective view of a 3D camera system using an LED array for sequential pattern projection, according to one exemplary embodiment.
Figure 17:
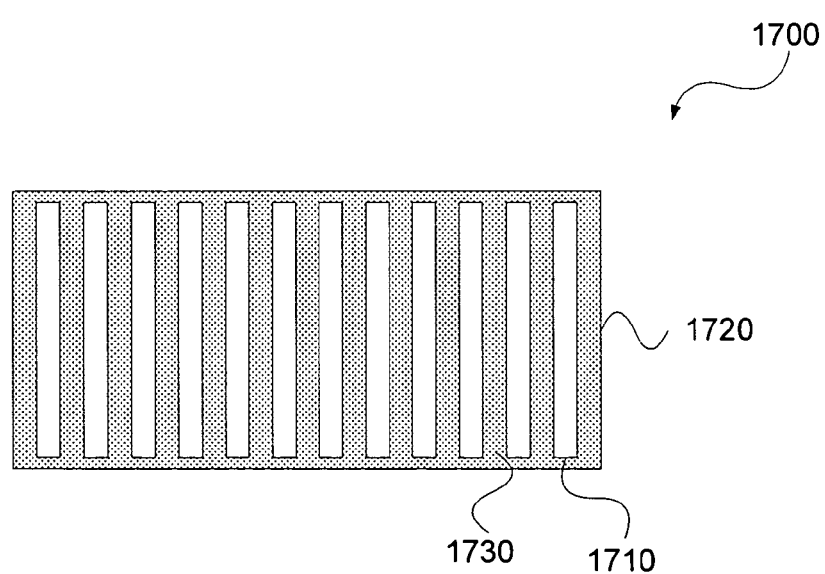
FIG. 17 is a frontal view of a slot plate configuration, according to one exemplary embodiment.

FIG. 16 shows a setup of a 3D Camera using LED array. As illustrated in FIG. 16, the setup using the LED array (1600) includes a number of driver electronics (1520) coupled to an array of closely spaced RGB LEDs (1510) formed in a video projector. The light produced by the array of RGP LEDs (1510) passes through a number of narrow-band pattern projections (1540, 1550, 1560) and onto the desired object (1450). The produced images are then collected by a monochromatic CCD camera (1440) and saved, integrated, and displayed on a computing device (1610) or other display device.

Implement Sequential Projection Using Slot Plate

Rather than using an optical filter as described above, a flat plate (1720) with slots (1710) formed therein will generate an intensity varying illumination pattern. The slotted plate (1700) can be made of any non-transparent material, and there is in no way limited to a particular physical dimension of the plate (1720). Rather, according to one exemplary embodiment, the width of each slot (1710) is the same as the width of the bars (1730) between the slots. Further, there is no dimensional requirement on the thickness of the plate (1720). Utilization of the slotted plate (1700) will reduce the cost of the present exemplary system when compared to the cost associated with LVWFs. The image formatting mechanism associated with incorporating a slot plate (1700) is described in detail below.

According to Huygens' wave theory of light, each point on a wave front of light acts as a source for a new spherical wave, and the illumination intensity on the surface of an object can be expressed as an integral function of all the point light sources. In the case of the slot plate (1700), light sources are the light penetrating through the slots (1710) on the plate (1720); therefore, the intensity function can be expressed as:

$$\text{Intensity}(l) = \int_s I(s, l) ds$$

where s is the spatial location of the point light sources on the slot plate (1700), l is the spatial location on the surface of the object, I(s, l) is the illumination intensity on the surface of the object at the l location produced by individual point light source of s. Accumulation of contributions from all the point light sources penetrating through the slot plate (1700) will produce the local intensity on the object surface point l.

Figure 18:
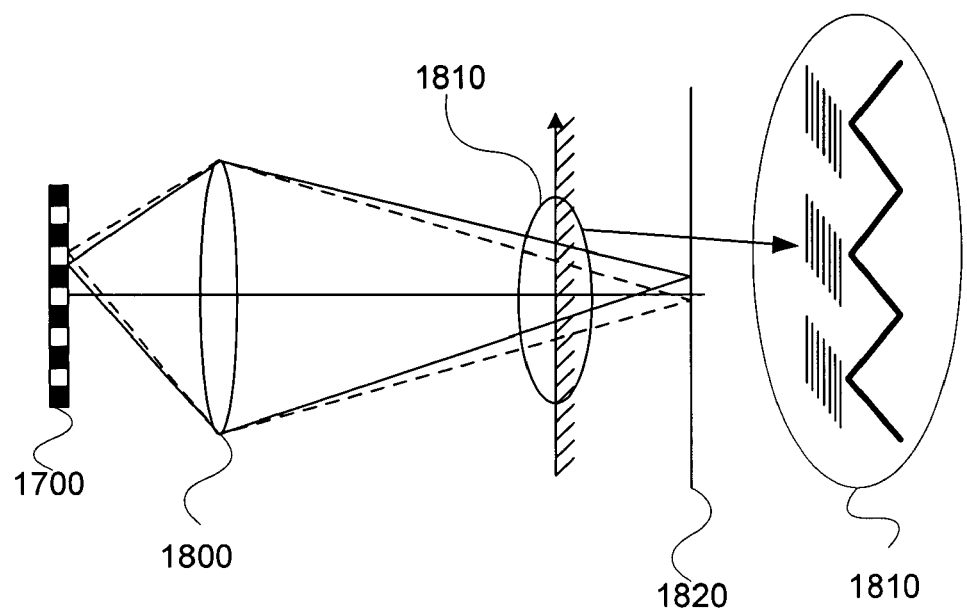
FIG. 18 is a block diagram illustrating an image formation mechanism of a zigzag pattern using a slot plate, according to one exemplary embodiment.

FIG. 18 illustrates the zigzag intensity pattern formation process. As illustrated in FIG. 18, light passes through the slot plate (1700) and passes through a projection lens (1800). The light is then focused on an object surface point l, in front of the imaging plane of the slot plate (1820). As mentioned above, proper control of the relative position of the projector and the object surface allows the production of a zigzag waveform (1810) on the surface of the object being imaged.

MRP Embodiment

According to one exemplary embodiment, the above-mentioned slot-plate characteristics are combined with a micro-switching mechanism to implement the small phase shift of the zigzag pattern (1810). As shown in FIG. 13, three patterns can be combined to form the multi-rainbow projection.

Figure 19:
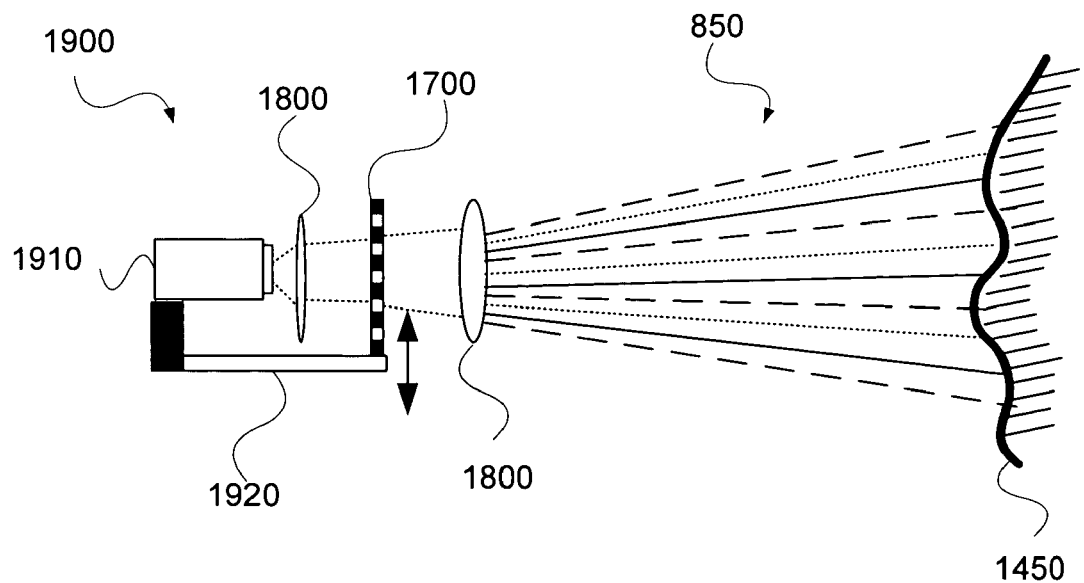
FIG. 19 is a block diagram illustrating a micro-shifting of the slot plate using a bi-morpher material, according to one exemplary embodiment.

According to the exemplary embodiment illustrated in FIG. 19, a micro shifting design is shown using a piece of bimorpher material (1920) to facilitate the micro-switching of the slot plate (1700). Bimorpher materials have the unique property of the electrical field induced motion. By fixing one end of the bimorpher mateiral (1920), the other end of the bimorpher can be controlled to move transversally by applying DC voltage on the two sides of the bimorpher plate. According to one exemplary embodiment, a bimorpher piece (1920) is fixed on the light source (1910) and the slot plate (1700) is controlled to move transversally relative to the position of the light source. According to this exemplary embodiment, the zigzag pattern generated by the light source (1910) and slot plate (1700) via the optical lenses (1800) can be shifted on the surface of the object being imaged (1450) to form an MRP design (850).

Figure 20:
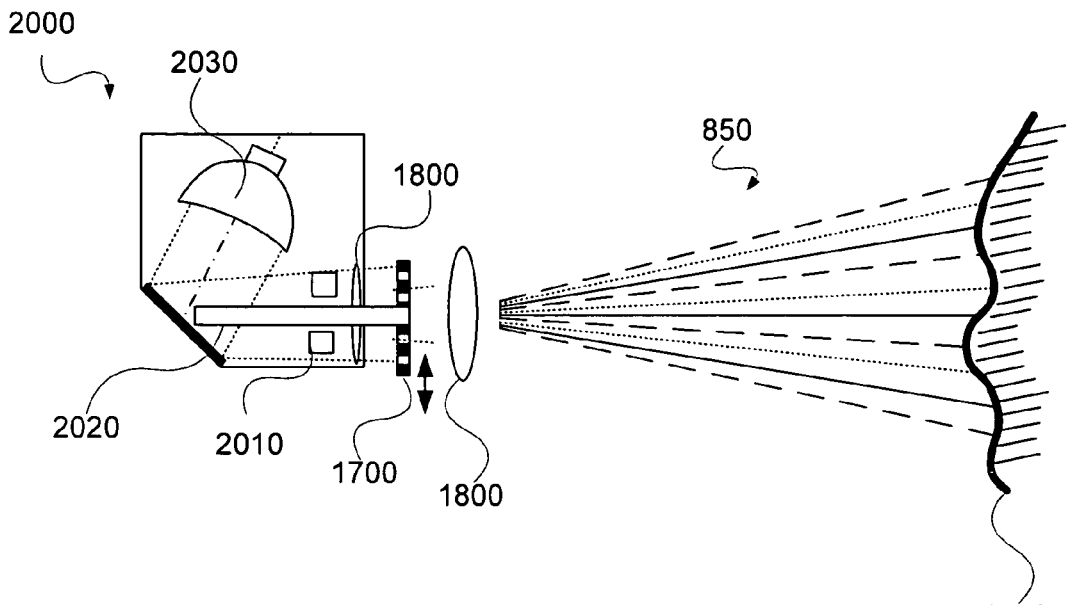
FIG. 20 is a block diagram illustrating a micro-switching mechanism used to move the slotted plate into multiple positions, according to one exemplary embodiment.

Similarly, FIG. 20 illustrates another exemplary design of the micro-switching mechanism (2000) that employs a cantilever beam (2020) having a plurality of solenoid actuators (2010) disposed adjacent thereto. According to the exemplary embodiment illustrated in FIG. 20, when none of the actuators (2010) are activated, the cantilever beam (2020) remains in its neutral position illustrated in FIG. 20. However, when the solenoid actuators are selectively activated, the cantilevered beam (2020) moves to a corresponding position. Since the cantilevered beam (2020) is connected to the slot plate (1700), the relative motion of the cantilevered beam produces a corresponding motion of the slot plate. Alternating activation of the solenoids (2010) can achieve three or more different positions for the slot plate using only a set of very simple and inexpensive components. Additionally, the control signal is binary and can be generated using a digital port of a host PC or other controlling device. As a result of the above-mentioned selective activation of the solenoid actuators (2010), the micro-switching system (2000), according to one exemplary embodiment, directs light produced by a light source (2030), focuses it through the slot plate (1700), and produces an MRP design on an object being imaged (1450).

SWIFT Embodiment

While the above-mentioned methods reduce manufacturing costs by implementing a 3-chip CCD sensor to collect a number of monochromatic images, a number of issues may arise from the use of a 3-chip CCD sensor. One issue that often arises with the use of a 3-chip CCD sensor is known as "cross-talk." Traditional 3-chip CCD sensors use a single "exposure trigger" signal line for all 3 CCD sensors. An exposure trigger is a period of time wherein a light projection is exposed to its corresponding sensor channel. Images with all three colors were traditionally taken during the same exposure period. This of course creates the possibility of crosstalk among these channels. Crosstalk occurs when multiple components of light exposure contribute to a single component channel. For example, the output of the Red channels will not only be contributed to by the red component of the light exposure, but also the "crosstalk" from blue spectrum due to the spectrum sensitivity curve of the red sensor. The fundamental reason for the crosstalk is the fact that multiple channels of lighting pattern are shined to the sensor simultaneously. If these lighting patterns are projected in a sequential fashion within the same field cycle, the crosstalk problem can be resolved.

Figure 21:
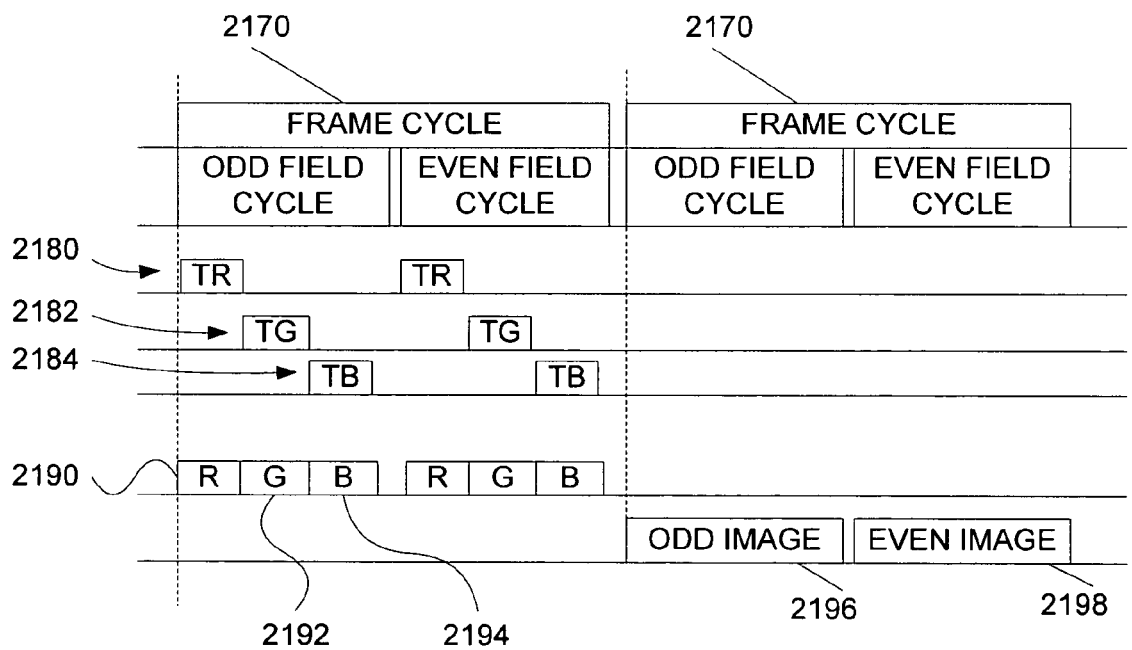
FIG. 21 is a chart illustrating a sequential with in frame time (SWIFT) imaging method, according to one exemplary embodiment.

FIG. 21 illustrates an implementation of a sequential within frame time (SWIFT) concept according to one exemplary embodiment. As illustrated in FIG. 21, rather than using single exposure trigger timing, a plurality of timing trigger circuits are used to produce separate and independent exposure trigger signals (2180, 2182, 2184) for red, green, and blue channels, respectively. These trigger signals TR (2180), TG (2182), and TB (2184) are synchronized with their corresponding light source/structural pattern projections for Red (2190), Green (2192), and Blue (2194) strobe channels. The trigger signals corresponding to sensor exposure (2180, 2182, 2184) as well as the light source projections (2190, 2192, 2194) can be overlapping or non-overlapping, depending on the tolerance of different channels for being affected by crosstalk. For example, if red (2190) and green (2192) channels have little crosstalk, they can be controlled to be exposed simultaneously. On the other hand, if red (2192) and blue (2194) have severe crosstalk, then their timing should be arranged sequentially to eliminate the possible crosstalk effect.

More importantly, the duration of these trigger signals TR (2180), TG (2182), and TB (2184) can be controlled independently to accommodate the CCD sensitivity, object reflectivity for different surface colors, and illumination source variations. The light source/structural pattern projections for red (2190), green (2192), and blue (2194) channels will be controlled accordingly to synchronize with the exposures of their corresponding channels.

By synchronizing the projection and exposure trigger signals as illustrated above, high image collection rates may be achieved. The above-mentioned synchronization methods facilitate three-dimensional imaging acquisition at typical video rates (30 frames per second). Additionally, the exposure time for each exposure trigger can be much shorter (e.g. 1/2000 sec.) than the 1/30 of a second frame cycle (2170) allowing all of the exposures for different channels to be performed within a single frame cycle (2170). Moreover, because the projection and exposure trigger signals may be sequentially synchronized, crosstalk issues may be eliminated and the design of the multi-spectrum projection mechanism may be simplified. Additionally, both odd (2196) and even images (2198) may be produced in a single frame cycle (2170).

Simultaneous Acquisition of Full Coverage 3D Image

Figure 22:
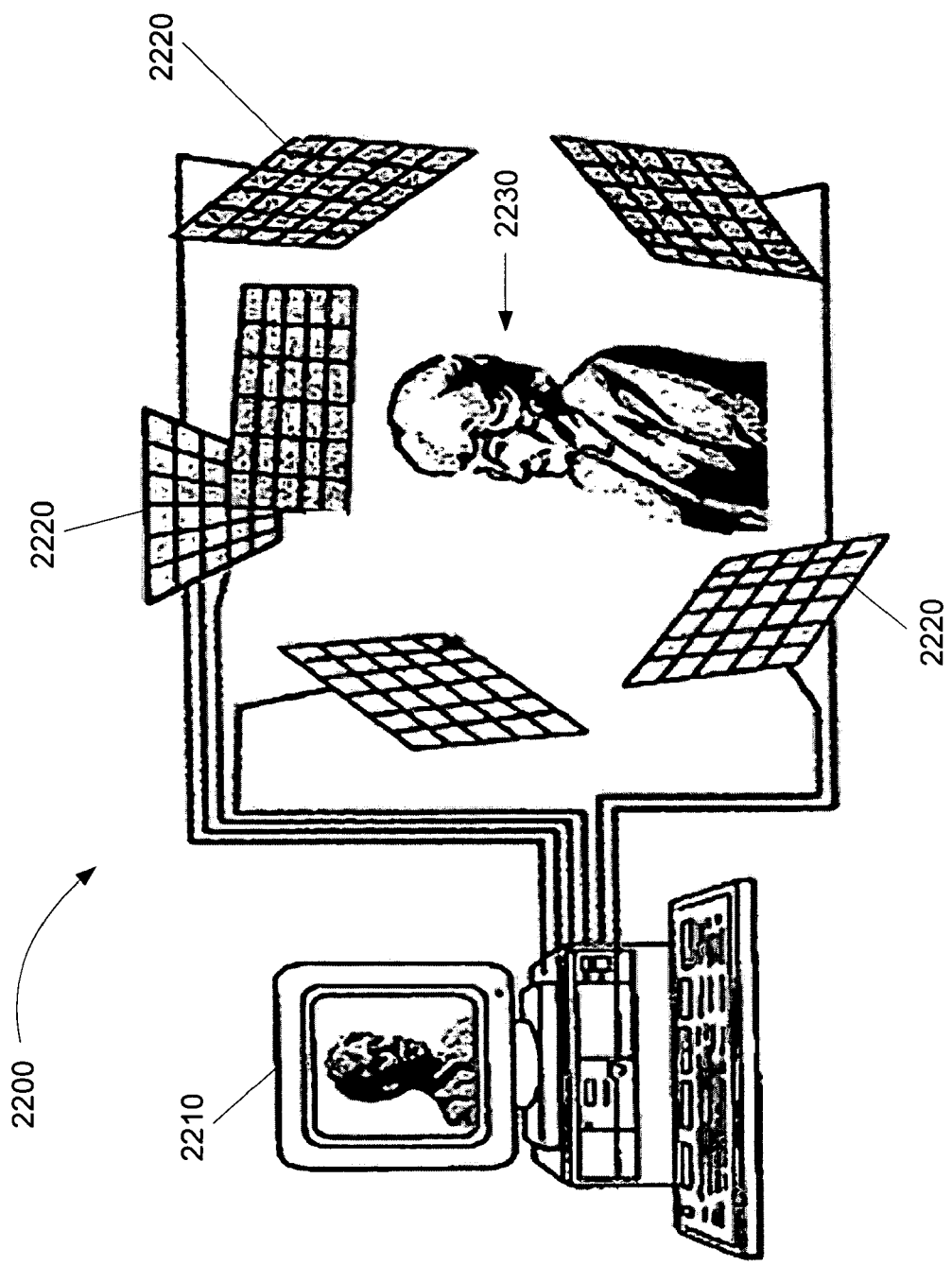
FIG. 22 is a perspective view illustrating a simultaneous acquisition of multiple 3D images from different views, according to one exemplary embodiment.

Incorporating the above-mentioned teachings, an instant full head 3D imaging system may be developed as illustrated in FIG. 22. The key for the instant full head 3D imaging system is the "snapshot" instant acquisition of multiple images from different views to achieve full head coverage, which may present a challenge for interfacing the operations of multiple 3D cameras.

In order to remedy the potential crosstalk problems associated with full coverage of a 3D image using multiple cameras, a matched narrow-band spectral filter may be placed in front of each CCD sensor (2220) causing each 3D camera to function at a pre-designed wavelength range. As shown in FIG. 22, a system (2200) is presented including multiple 3D cameras having sensors (2220) with different non-overlapping bandwidths positioned around an object to be imaged (2230). Each sensor (2220) may collect 3D data regarding the object to be imaged (2230) from different views using the above-mentioned high speed imaging methods. For example, once the object to be imaged (2230) is positioned, multiple light patterns may be simultaneously projected onto the object to be imaged and the sensor (2220) of each 3D camera may then simultaneously acquire images without interfering with each other. According to the teachings previously mentioned, each sensor (2220) may use a different bandwidth to eliminate crosstalk between images, similar to dense wavelength division multiplexing (DWDM). Once acquired, the images may then be routed to a computing device (2210) where they are compiled to form a full surface image.

Integrated 3D Imaging System Using Sequential Projection

Figure 23:
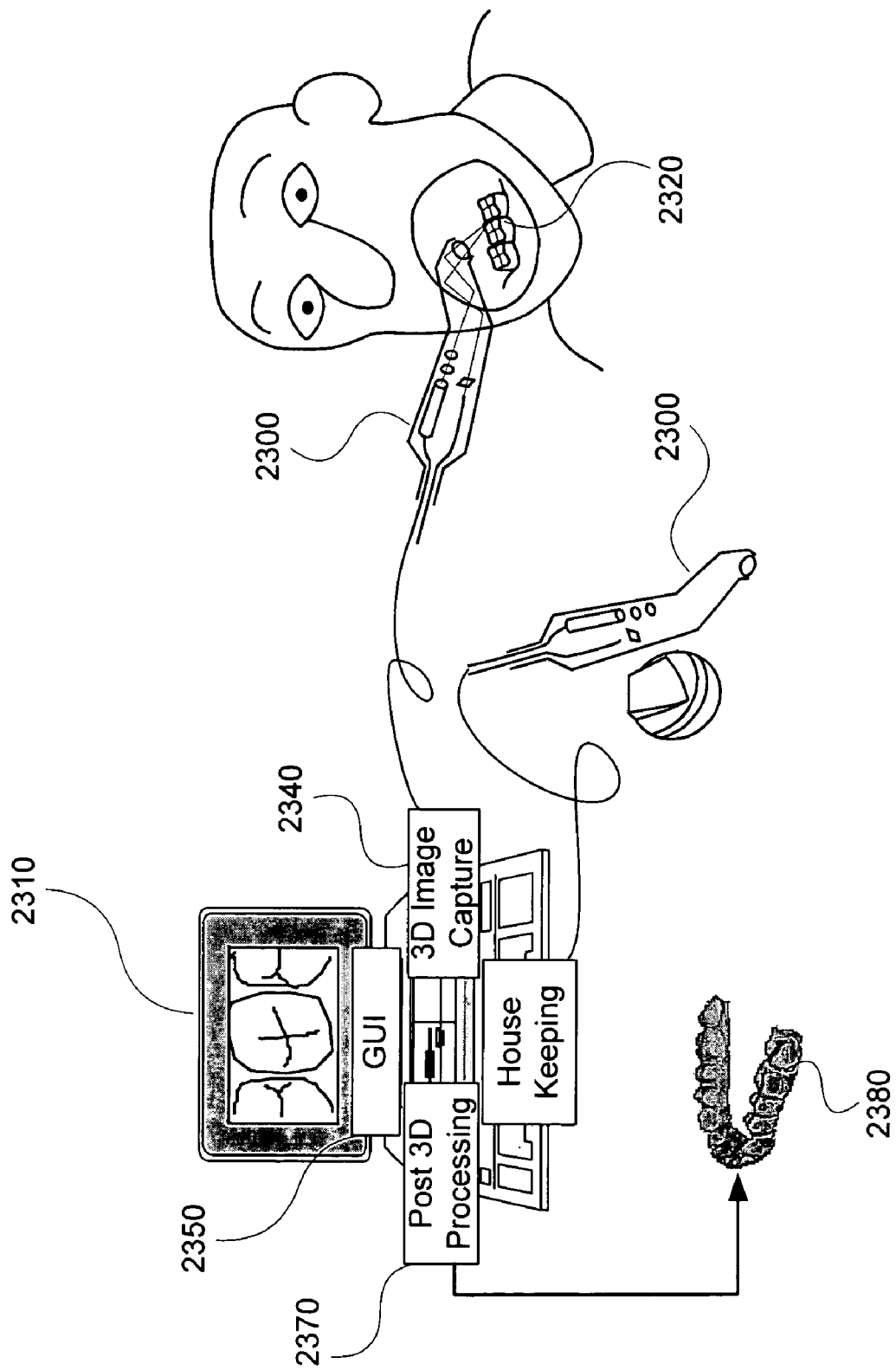
FIG. 23 is a system diagram illustrating a 3D imaging system applied to an intraoral 3D camera, according to one exemplary embodiment.

According to one exemplary embodiment, the above-mentioned 3D imaging system may incorporate sequential projecting imaging in an integrated 3D imaging system. FIG. 23 illustrates an operational flowchart showing how a handheld imaging system may incorporate the present exemplary system and method to perform dental imaging. As illustrated in FIG. 23, the dentist or other user will place a disposable cover on the handheld camera and activate control software that is present on a computing device (2310) communicatively coupled to the handheld camera (2300).

When performing a single capture sequence, an operator will point the handheld camera (2300) toward the tooth (2320) or other object being imaged. The operator may then trigger the handheld camera (2300) using any number of trigger activation methods including, but in no way limited to, finger operation or voice command. Once triggered, the handheld camera (2300) may delay for a short period to eliminate hand movement due to pushing button, etc. and then begins to capture three frames of images. During the image capturing process, an indicator light flashes to indicate the process of image capture.

Once the capturing process (2340) is completed, a single beep or other signal may be activated and the indicator light changes to solid. A preview 3D image is calculated "on the fly", and it displays on the graphical user interface (2350) with approximate position registration. The operator then determines if the image quality is acceptable. If not, the operator re-takes the same image. If the image quality is acceptable, the system will pursue the next imaging process.

In contrast to the above-mentioned single capture sequence, a multiple capture sequence may be performed using the handheld camera (2300). According to this multiple capture sequence, a multiple capture command may be initiated and the user points the handheld camera (2300) toward the tooth (2320) or other object being imaged. The operator again triggers the handheld camera (2300) using any number of trigger activation methods including, but in no way limited to, finger operation or voice command. Once triggered, the handheld camera (2300) may delay for a short period to eliminate hand movement due to pushing button, etc. and then begins to capture three frames of images. During the capturing process (2340), an indicator light may flash.

Once the capturing process (2340) is completed, a single beep may sound and the indicator light may change to solid or otherwise signal completion of the requested capturing process. The operator may then provide another capture command causing the system to capture another image according to the method illustrated above. This sequence continues until the operator pushes the trigger button again or otherwise causes the cessation of the process.

Additionally, as illustrated in FIG. 23, the 3D model generated by the above-mentioned method may go through a viewing operation provided by a graphical user interface (2350) and provide information to be used by a post-processing operation (2370). According to one exemplary embodiment, the post-processing operation may use the collected 3D data to produce a casting or other physical representation of the imaged tooth (2320).

Figure 24:
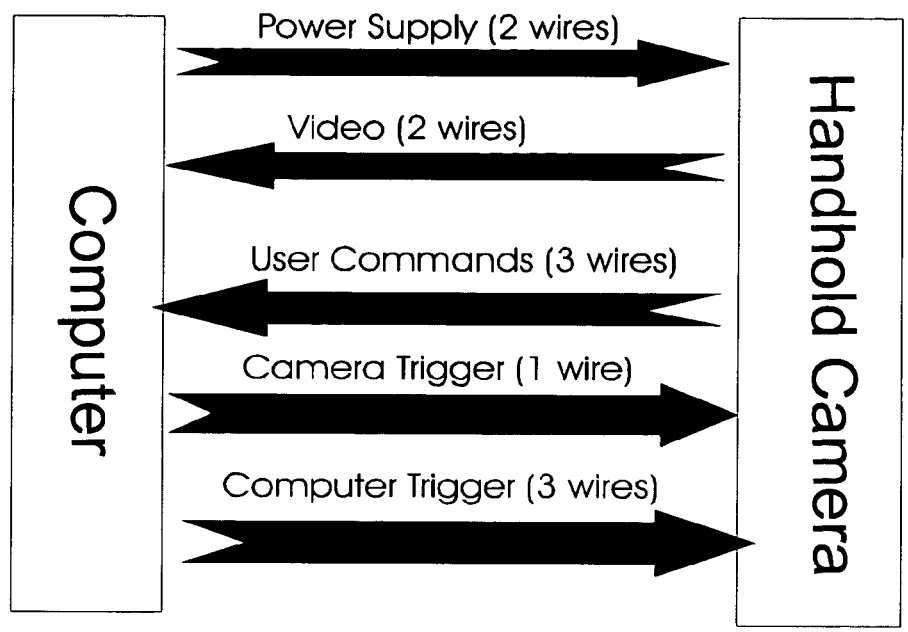
FIG. 24 is a communication protocol diagram illustrating a communication contact between a handheld camera and a host computer, according to one exemplary embodiment.
Figure 25:
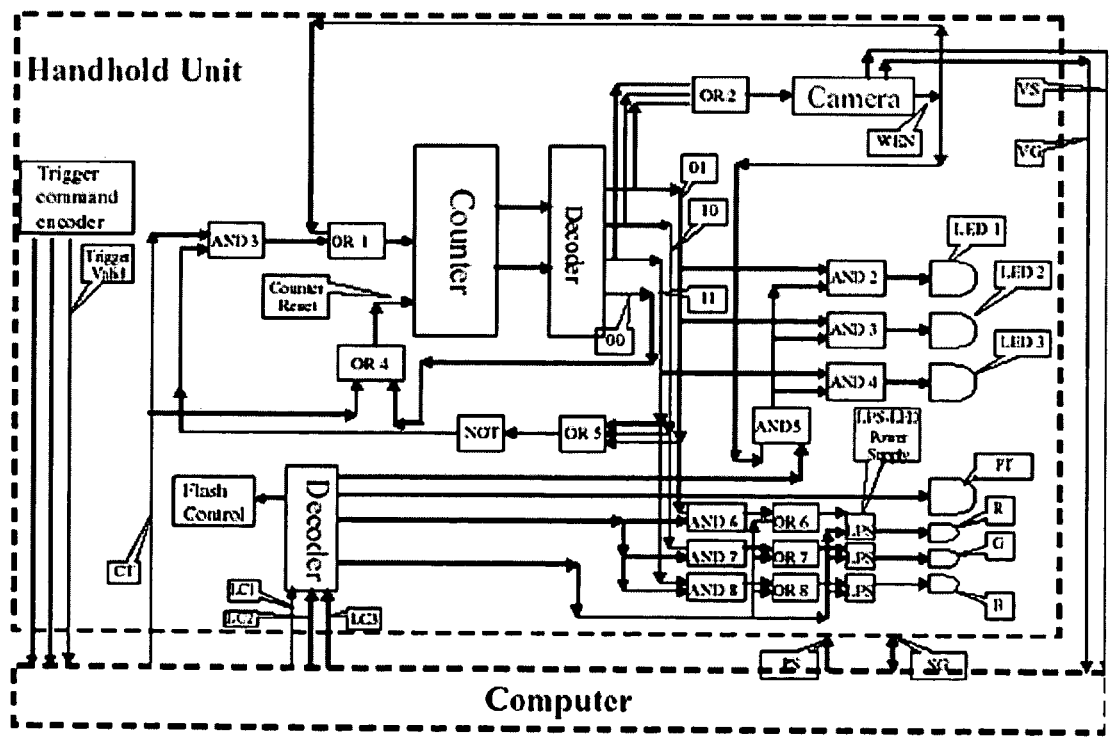
FIG. 25 is a control logic diagram illustrating the internal logic of an intraoral 3D camera, according to one exemplary embodiment.
Figure 26:
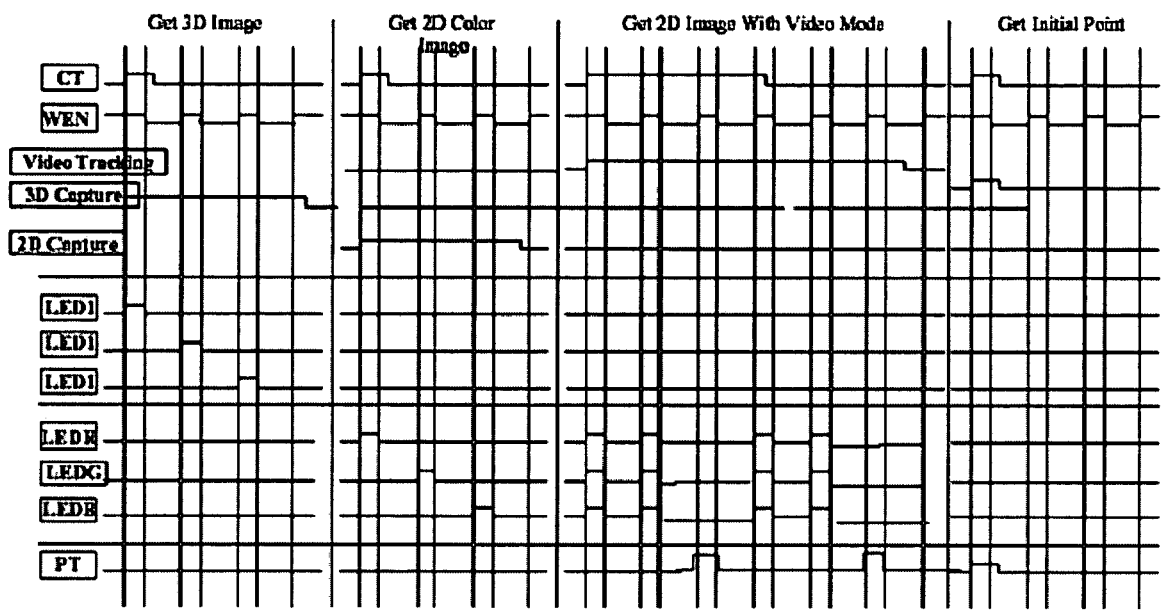
FIG. 26 is a timing diagram illustrating an intraoral 3D camera control timing scheme, according to one exemplary embodiment.

FIG. 24 illustrates the communicative connection established between the handheld 3D camera (2300) and the computing device (2310) according to one exemplary embodiment. As illustrated in FIG. 24, the handheld 3D camera (2300) may receive a power supply, a camera trigger, and a computer trigger from the computing device (2310). Similarly, the computing device (2310) may receive a video signal and user commands via the handheld 3D camera (2300) to provide the above-mentioned functions. An exemplary control logic that may be incorporated by the above-mentioned handheld 3D camera (2300) is shown in FIG. 25 with an exemplary timing diagram illustrated in FIG. 26.

Using Sequential Projection to Acquire Color Image from Monochromic Sensor

Figure 27:
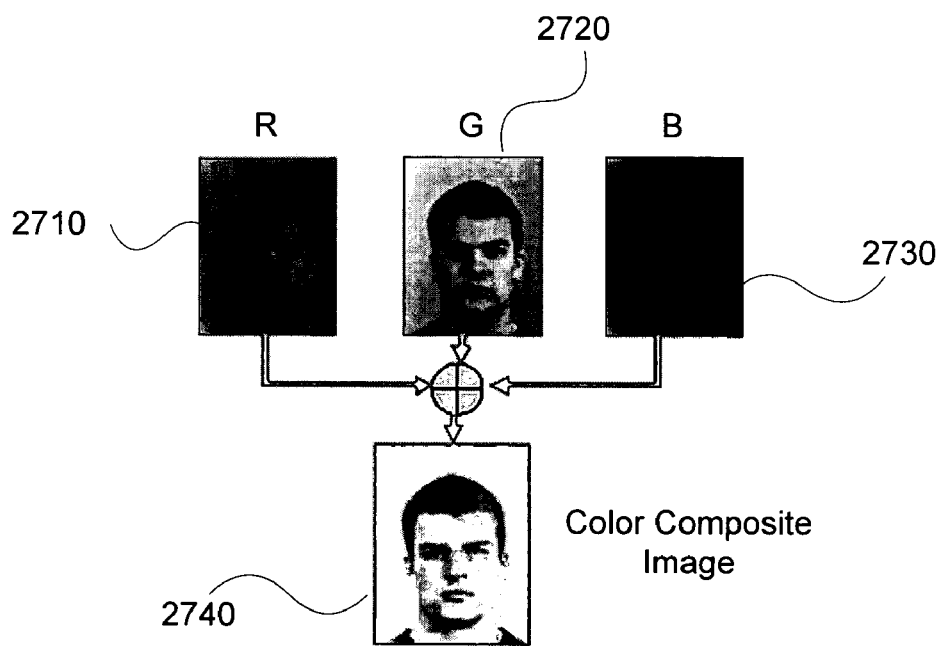
FIG. 27 is a method diagram illustrating the combination of three sequential images to produce a composite true color image, according to one exemplary embodiment.

While the above-mentioned system and method are described in the context of a monochromatic sensor, one exemplary embodiment allows the acquisition of a color image using a monochromatic sensor, as will be described in further detail below. According to one exemplary embodiment, three color illumination sources (R,G,B LEDs for example) are used to expose an object being imaged. According to this exemplary embodiment, three sequential images under three different colors of lighting can be acquired and then combined to produce a true color composite image, as illustrated in FIG. 27. As shown in FIG. 27, an image collected using a red illumination source (2710), an image collected using a green illumination source (2720), and an image collected using a blue illumination source (2730) may be combined to form a composite color image (2740) of the object being imaged.

According to the exemplary embodiment illustrated in FIG. 27, selection of the light sources to produce the RGB images will vary the full color fidelity of the composite color image (2740). Consequently, the composite color image is enhanced if the color spectrum of the selected light sources is as close as possible to the three primary colors. In an alternative embodiment, if the object being imaged does not exhibit a reflectivity of the full spectrum, alternative spectrums may be used to better match the reflection of the surface being imaged.

Implementation of Sequential Projection Mechanism

According to one exemplary embodiment, the sequential projection mechanism may be incorporated into a facial imaging system that can acquire 3D facial images in real-time continuously, without projecting visible lights on to the subject, and without being affected by ambient visible illumination. FIG. 8 illustrates the originally proposed Multi-Rainbow Projection (MRP) implementation strategy using the spectral-multiplex design. With proper spectral beamsplitters (830) placed at 45-degree angles across the optical path, three identical intensity filters with a saw-tooth pattern may be used to produce a three-color MRP illumination. The dichroic filters (820, 822, 824) will selectively transmit/reflect spectral bands properly to generate MRP patterns (850). Additionally, three light projectors (810, 812, 814) can share the same white light source, either via optical fiber or via proper relay optics.

While the present exemplary system and method is described using visible RGB colors, the same principle applies to other spectrum bands. In fact, according to one exemplary embodiment, to make the image acquisition process invisible to the subjects, IR projections from 700 nm to 1200 nm may be employed.

Figure 28:
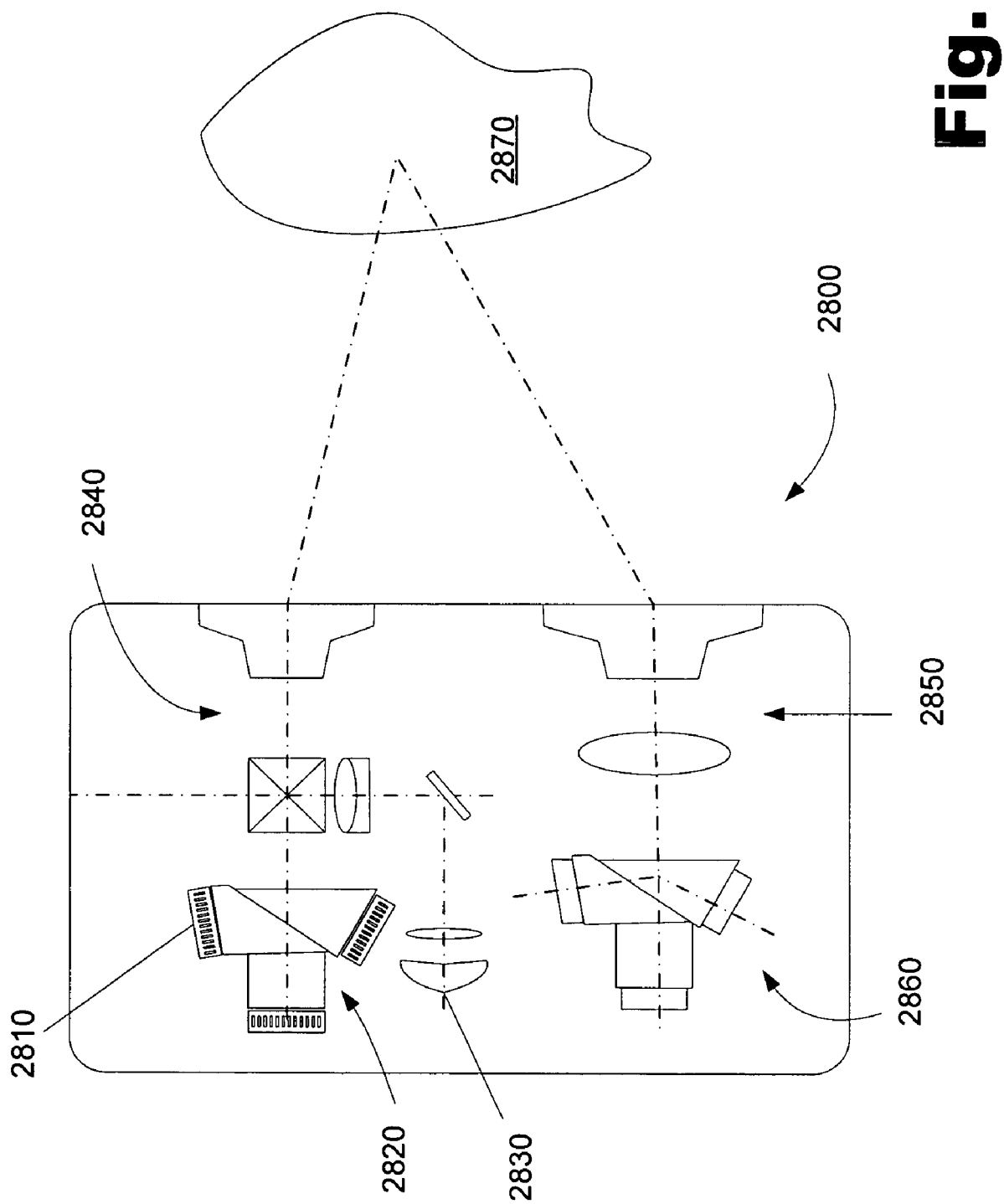
FIG. 28 is a simple block diagram illustrating the components of a visible or near infrared rainbow 3D camera, according to one exemplary embodiment.

FIG. 28 illustrates an exemplary system that may be used to acquire 3D images in real-time without projecting visible light on the subject according to one exemplary embodiment. As shown in FIG. 28, an exemplary 3D imaging system (2800) is equipped with a near infrared (NIR) Rainbow light source (2830) such as a halogen lamp with a long pass filter, a plurality of mirrors with a saw-tooth reflection pattern (2810), Philips prisms (2820), and other projection optics (2840) including a polarizing beam splitter. Similarly, the imaging portion of the 3D imaging system (2800) illustrated in FIG. 28 includes imaging optics (2850) such as lenses and Philips prisms as well as three NIR CCD sensors (2860). Because identical Philips prisms may be used in both the sensors (2860) and the light source optics, design and production costs of the NIR 3D imaging system (2800) illustrated in FIG. 28 are reduced.

Using the configuration illustrated in FIG. 28, matching spectrum bands between the 3CCD sensor (2860) and the light source (2830) is facilitated by the fact that both the projection and the imaging are performed using identical prisms. Additionally, any number of wavelengths from the NIR spectrum may be used, as long as three bands can be separated, and sawtooth intensities are generated by three identical "mirror gratings," with ⅓ phase shift.

In conclusion, the present system and method provides a number of exemplary systems and methods for using sequential frame image acquisitions to obtain equivalent rainbow projection information such that a 3D profile of the object surface can be computed accurately. Additionally, the use and advantages of a multi-rainbow projection (MRP) were disclosed. The distinctive advantages of this new method include its ability to use low-cost monochromic imaging sensor (instead of high quality and expensive color imaging sensor) to acquire rainbow projection pattern. This method also allows for the use of monochromic projection pattern filters to generate the required illumination, reducing the cost of optical system fabrication thus making the overall 3D imaging system affordable with increased precision.

What is claimed is:

1. A method for acquiring a three-dimensional (3D) surface profile data set of an object comprising:
   with a light source, illuminating a surface of said object with a pattern of light that varies spatially by wavelength such that at least one visible spectrum of light arranged in a rainbow pattern occurs in illumination of said surface;
   capturing light reflected from said object with a monochromatic camera;
   sequentially disposing each of a plurality of different color filters on said monochromatic camera such that output from said monochromatic camera is combined into a color image; and
   calculating 3D data (X, Y, Z) for each visible point on said object based upon triangulation in which each wavelength in said visible spectrum corresponds to an angle with respect to a baseline between said light source and said camera.

2. The method of claim 1, wherein said illuminating comprises generating a multi-rainbow projection pattern in which multiple visible spectra are repeated side by side across said surface.

3. The method of claim 2, wherein said generating a multi-rainbow projection pattern comprises projecting white light thru a multi rainbow filter toward said object.

4. The method of claim 2, wherein said generating a multi-rainbow projection pattern comprises:
   sequentially activating a plurality of color lights; and
   combining light from said color lights to form said multi-rainbow projection pattern.

5. The method of claim 4, wherein said sequentially activating a plurality of colored lights comprises sequencing an array of primary color lights.

6. The method of claim 5, wherein said primary color lights comprise light emitting diodes (LED).

7. The method of claim 1, wherein said camera comprises a charge coupled device (CCD).

8. The method of claim 1, wherein said capturing light reflected from said object comprises selectively generating a 2 dimensional or a 3 dimensional picture.

9. The method of claim 1, wherein said calculating 3D data (X, Y, Z) for each visible point on said object comprises restricting a search space to a single cycle of said rainbow pattern.

10. The method of claim 9, further comprising identifying an initial point determination based on a neighboring correct match.

11. The method of claim 1, wherein said calculating 3D data for each visible point on said object comprises utilizing a lookup table for color to angle matching.

12. The method of claim 1, further comprising:
   positioning a red filter on said monochromatic camera to capture a first image;
   positioning a green filter on said monochromatic camera to capture a second image;
   positioning a blue filter on said monochromatic camera to capture a third image; and
   combining said first, second, and third image into a single RGB image.

13. The method of claim 1, wherein said illuminating a surface of said object comprises activating a light emitting diode (LED) array.

14. The method of claim 13, wherein said activating a light emitting diode (LED) array comprises synchronizing said LED array activation with placement of each of said color filters on said camera.

15. The method of claim 13, wherein said activating an LED array comprises projecting high power illumination for approximately 1/1000 of a second.

16. The method of claim 1, wherein said camera captures 120 frames per second, each frame being captured with a different color filter than a preceding frame to produce 30 color frames per second.

17. A system for acquiring a three-dimensional (3D) surface profile of an object or scene comprising:
   a means for illuminating said object or scene with a pattern of light that varies spatially by wavelength such that at least one visible spectrum of light arranged in a rainbow pattern occurs in illumination of said object or scene;
   a monochromatic sensor means for capturing a light reflected from said object or scene;
   means for sequentially disposing each of a plurality of different color filters on said sensor means such that output from said monochromatic sensor means is combined into a color image; and
   a means for calculating 3D data coordinates for each visible point on said object or scene based upon triangulation in which each wavelength in said visible spectrum corresponds to an angle with respect to a baseline between said light source and said camera.

18. The system of claim 17, wherein said illumination means comprises a plurality of lights of different primary colors.

19. The system of claim 18, further comprising an optical means for combining radiation from said plurality of lights to form a multi rainbow projection pattern.

20. The system of claim 17, wherein said illumination means comprises an LED array.

21. The system of claim 20, further comprising means for synchronizing said LED array with said sensor means.

22. The method of claim 17, wherein said array of LEDs comprises red, green and blue LEDs.

* * * * *